(12) United States Patent
Khaleghi

(10) Patent No.: US 10,484,845 B2
(45) Date of Patent: Nov. 19, 2019

(54) ELECTRONIC NOTEBOOK SYSTEM

(71) Applicant: Karen Elaine Khaleghi, Pacific Palisades, CA (US)

(72) Inventor: Karen Elaine Khaleghi, Pacific Palisades, CA (US)

( * ) Notice: Subject to any disclaimer, the term of this patent is extended or adjusted under 35 U.S.C. 154(b) by 0 days.

(21) Appl. No.: 16/250,279

(22) Filed: Jan. 17, 2019

(65) Prior Publication Data

US 2019/0149962 A1    May 16, 2019

Related U.S. Application Data

(63) Continuation of application No. 15/988,191, filed on May 24, 2018, now Pat. No. 10,187,762, which is a
(Continued)

(51) Int. Cl.
*H04W 4/14* (2009.01)
*G10L 15/26* (2006.01)
(Continued)

(52) U.S. Cl.
CPC ............ *H04W 4/14* (2013.01); *G06F 3/0487* (2013.01); *G06F 17/277* (2013.01);
(Continued)

(58) Field of Classification Search
CPC ...... H04W 4/14; G06F 3/0487; G06F 17/277; G06F 17/2775; G06F 19/00; G10L 15/26; G10L 25/63; G10L 25/72
See application file for complete search history.

(56) References Cited

U.S. PATENT DOCUMENTS 3,594,066 A * 7/1971 Cook ..................... G02B 15/14
                                                359/684
3,649,765 A    3/1972 Rabiner
(Continued)

OTHER PUBLICATIONS

Matheson, "Watch Your Tone—Voice-Analytics Software Helps Customer-Service Reps Build Better 2 Rapport with Customers," MIT News Office, httg://news.mit.edu/2016/startup-cogito-voice-analyticscall-centers-otsd-0120; Jan. 20, 2016; 4 pages.
(Continued)

*Primary Examiner* — Jung-Mu T Chuang
(74) *Attorney, Agent, or Firm* — Knobbe, Martens, Olson & Bear LLP

(57) ABSTRACT

An electronic notebook system is described that comprises a housing, a computing device, wireless interfaces, antennas, sensors, a touch display configured to receive input via a stylus and/or human digit input, the stylus comprising a pressure and/or an inclination sensor, a microphone, camera, the notebook system configured to provide a user condition interface, receive a user selection of a first user condition, provide an interface configured to receive user details, receive audible user details via the microphone, convert the audible user details received via the microphone to text, perform natural language processing to identify text keywords utilizing sentence segmentation, part-of-speech tagging, paraphrase recognition, and/or co-reference resolution, identify a condition based at least in part on the identified one or more keywords, dynamically generate an alert based at least in part on the identified condition, wirelessly transmit the generated alert to one or more destinations via at least a first wireless interface and antenna.

29 Claims, 32 Drawing Sheets

Related U.S. Application Data continuation of application No. 15/862,552, filed on Jan. 4, 2018, now Pat. No. 10,014,004, which is a continuation of application No. 15/198,762, filed on Jun. 30, 2016, now Pat. No. 9,899,038.

(51) Int. Cl.

| | | |
|---|---|---|
| *G06F 17/27* | (2006.01) | |
| *G06F 19/00* | (2018.01) | |
| *G06F 3/0487* | (2013.01) | |
| *G10L 25/63* | (2013.01) | |
| *G10L 25/72* | (2013.01) | |
| *G16H 80/00* | (2018.01) | |
| *G16H 40/63* | (2018.01) | |
| *G16H 40/67* | (2018.01) | |
| *G16H 50/30* | (2018.01) | |
| *G16H 50/20* | (2018.01) | |
| G10L 15/22 | (2006.01) | |
| G16H 40/20 | (2018.01) | |
| G16H 20/00 | (2018.01) | |

(52) U.S. Cl.
CPC .......... *G06F 17/2775* (2013.01); *G06F 19/00* (2013.01); *G10L 15/26* (2013.01); *G10L 25/63* (2013.01); *G10L 25/72* (2013.01); *G16H 40/63* (2018.01); *G16H 40/67* (2018.01); *G16H 50/20* (2018.01); *G16H 50/30* (2018.01); *G16H 80/00* (2018.01); *G10L 2015/225* (2013.01); *G16H 20/00* (2018.01); *G16H 40/20* (2018.01)

(56) References Cited

U.S. PATENT DOCUMENTS

| | | | | |
|---|---|---|---|---|
| 5,293,584 | A * | 3/1994 | Brown | G10L 15/18 |
| | | | | 704/200 |
| 5,633,910 | A | 5/1997 | Cohen | |
| 5,823,948 | A | 10/1998 | Ross, Jr. | |
| 5,924,074 | A | 7/1999 | Evans | |
| 6,039,688 | A | 3/2000 | Douglas | |
| 6,047,254 | A | 4/2000 | Ireton | |
| 6,234,964 | B1 | 5/2001 | Iliff | |
| 6,290,646 | B1 | 9/2001 | Cosentino | |
| 6,292,771 | B1 | 9/2001 | Haug | |
| 6,411,933 | B1 | 6/2002 | Maes | |
| 6,544,294 | B1 * | 4/2003 | Greenfield | G11B 27/034 |
| | | | | 715/234 |
| 6,941,271 | B1 | 9/2005 | Soong | |
| 7,302,490 | B1 * | 11/2007 | Gupta | H04N 21/2335 |
| | | | | 709/231 |
| 7,647,555 | B1 * | 1/2010 | Wilcox | G11B 27/11 |
| | | | | 715/721 |
| 7,770,117 | B1 * | 8/2010 | Uy | G11B 27/34 |
| | | | | 715/722 |
| 7,788,605 | B1 * | 8/2010 | Shoemaker | G11B 27/34 |
| | | | | 715/726 |
| 8,374,992 | B2 | 2/2013 | Meyyappan et al. | |
| 8,533,511 | B2 | 9/2013 | Ma et al. | |
| 8,606,595 | B2 * | 12/2013 | Udani | G06Q 10/105 |
| | | | | 705/2 |
| 8,775,213 | B2 * | 7/2014 | Hughes | G06Q 10/10 |
| | | | | 705/3 |
| 8,826,123 | B2 * | 9/2014 | Audet | G06F 17/241 |
| | | | | 715/243 |
| 9,158,335 | B2 | 10/2015 | Zheng | |
| 9,252,962 | B1 | 2/2016 | Valeti | |
| 9,256,588 | B1 | 2/2016 | Moscovich et al. | |
| 9,256,719 | B2 * | 2/2016 | Berini | G06F 21/32 |
| 9,305,155 | B1 * | 4/2016 | Vo | G06F 21/32 |
| 9,619,616 | B2 * | 4/2017 | Raduchel | H04W 8/18 |
| 9,658,756 | B2 | 5/2017 | Freeman | |
| 9,733,801 | B2 | 8/2017 | Audet | |
| 9,788,799 | B2 * | 10/2017 | Wagner | A61B 5/7278 |
| 9,899,038 | B2 | 2/2018 | Khaleghi | |
| 9,959,556 | B1 * | 5/2018 | Cordell | H04L 67/24 |
| 10,032,120 | B2 * | 7/2018 | Collins | G06Q 10/06 |
| 2002/0010679 | A1 * | 1/2002 | Felsher | G06F 19/328 |
| | | | | 705/51 |
| 2002/0012526 | A1 | 1/2002 | Sai | |
| 2002/0022975 | A1 | 2/2002 | Blasingame | |
| 2002/0026329 | A1 * | 2/2002 | Saito | G06F 19/325 |
| | | | | 705/3 |
| 2002/0035486 | A1 | 3/2002 | Huyn | |
| 2002/0062225 | A1 | 5/2002 | Siperco | |
| 2002/0082865 | A1 | 6/2002 | Bianco | |
| 2002/0116188 | A1 | 8/2002 | Amir | |
| 2002/0138271 | A1 | 9/2002 | Shaw | |
| 2002/0145742 | A1 | 10/2002 | Koenig et al. | |
| 2003/0115054 | A1 | 6/2003 | Iso-Sipila | |
| 2003/0140044 | A1 * | 7/2003 | Mok | G06Q 50/22 |
| 2004/0034869 | A1 * | 2/2004 | Wallace | G11B 27/034 |
| | | | | 725/45 |
| 2004/0059599 | A1 | 3/2004 | McIvor | |
| 2004/0133560 | A1 | 7/2004 | Simske | |
| 2004/0243443 | A1 | 12/2004 | Asano | |
| 2005/0055399 | A1 * | 3/2005 | Savchuk | H04L 63/0245 |
| | | | | 709/203 |
| 2005/0096906 | A1 | 5/2005 | Barzilay | |
| 2005/0137723 | A1 | 6/2005 | Liu | |
| 2005/0147214 | A1 | 7/2005 | Goerg et al. | |
| 2005/0149569 | A1 | 7/2005 | Hariharan et al. | |
| 2005/0165626 | A1 | 7/2005 | Karpf | |
| 2005/0172022 | A1 | 8/2005 | Brown | |
| 2006/0001666 | A1 | 1/2006 | Cake et al. | |
| 2006/0011399 | A1 | 1/2006 | Brockway et al. | |
| 2006/0047497 | A1 | 3/2006 | Chen | |
| 2006/0052674 | A1 | 3/2006 | Eisenstein | |
| 2007/0024454 | A1 | 2/2007 | Sinahal | |
| 2007/0074114 | A1 | 3/2007 | Adjali | |
| 2007/0168413 | A1 * | 7/2007 | Barletta | G06F 3/04883 |
| | | | | 709/203 |
| 2007/0216708 | A1 | 9/2007 | Mackay | |
| 2007/0276270 | A1 * | 11/2007 | Tran | A61B 5/0022 |
| | | | | 600/508 |
| 2008/0066973 | A1 | 3/2008 | Furuki | |
| 2008/0104048 | A1 | 5/2008 | Surendran | |
| 2008/0126426 | A1 | 5/2008 | Manas | |
| 2008/0133233 | A1 * | 6/2008 | Tsubura | G06Q 50/22 |
| | | | | 704/235 |
| 2008/0195495 | A1 | 8/2008 | Rubin et al. | |
| 2008/0301176 | A1 | 12/2008 | Fanelli et al. | |
| 2008/0313536 | A1 * | 12/2008 | Larsen | G06Q 10/06 |
| | | | | 715/273 |
| 2008/0319750 | A1 | 12/2008 | Potter | |
| 2009/0055735 | A1 | 2/2009 | Zaleski | |
| 2009/0077045 | A1 * | 3/2009 | Kirchmeier | G06Q 10/06 |
| 2009/0117922 | A1 | 5/2009 | Bell | |
| 2009/0292554 | A1 | 11/2009 | Schultz | |
| 2010/0034639 | A1 | 2/2010 | Moniz et al. | |
| 2010/0036871 | A1 | 2/2010 | Beckey et al. | |
| 2010/0037219 | A1 | 2/2010 | Chen et al. | |
| 2010/0076333 | A9 | 3/2010 | Burton | |
| 2010/0169108 | A1 * | 7/2010 | Karkanias | G06Q 50/22 |
| | | | | 705/2 |
| 2010/0228656 | A1 | 9/2010 | Wasserblat | |
| 2010/0262435 | A1 | 10/2010 | Smith | |
| 2010/0286490 | A1 * | 11/2010 | Koverzin | G06F 19/3418 |
| | | | | 600/301 |
| 2011/0040155 | A1 | 2/2011 | Guzak | |
| 2011/0068934 | A1 | 3/2011 | Weng et al. | |
| 2011/0091050 | A1 | 4/2011 | Hanai | |
| 2011/0148668 | A1 | 6/2011 | Li | |
| 2011/0184781 | A1 | 7/2011 | Hussam | |
| 2011/0202866 | A1 | 8/2011 | Huang | |
| 2012/0112879 | A1 | 5/2012 | Ekchian | |
| 2012/0198385 | A1 | 8/2012 | Audet | |
| 2012/0306648 | A1 | 12/2012 | Karaffa | |
| 2012/0306925 | A1 * | 12/2012 | Hwang | G06F 3/0488 |
| | | | | 345/647 |

(56) References Cited

U.S. PATENT DOCUMENTS

| | | | |
|---|---|---|---|
| 2012/0323589 A1* | 12/2012 | Udani | G06Q 10/105 705/2 |
| 2012/0323796 A1 | 12/2012 | Udani | |
| 2013/0009907 A1 | 1/2013 | Rosenberg | |
| 2013/0024206 A1* | 1/2013 | Hughes | G06Q 10/10 705/3 |
| 2013/0085781 A1 | 4/2013 | Navani | |
| 2013/0111331 A1 | 5/2013 | Rosen et al. | |
| 2013/0124192 A1 | 5/2013 | Lindmark | |
| 2013/0135095 A1 | 5/2013 | Stochita | |
| 2013/0163956 A1* | 6/2013 | Medhurst | G11B 27/031 386/241 |
| 2013/0185071 A1 | 7/2013 | Chen | |
| 2013/0257777 A1 | 10/2013 | Benko | |
| 2013/0275151 A1* | 10/2013 | Moore | G06Q 10/10 705/3 |
| 2013/0325493 A1 | 12/2013 | Wong | |
| 2014/0019119 A1 | 1/2014 | Liu | |
| 2014/0068489 A1 | 3/2014 | Wyland | |
| 2014/0074454 A1 | 3/2014 | Brown | |
| 2014/0081667 A1* | 3/2014 | Joao | G06F 19/328 705/3 |
| 2014/0143671 A1 | 5/2014 | Kovalick | |
| 2014/0164310 A1* | 6/2014 | Chen | G06N 5/025 706/47 |
| 2014/0164784 A1* | 6/2014 | Sinderbrand | G06F 21/602 713/189 |
| 2014/0172707 A1 | 6/2014 | Kuntagod | |
| 2014/0195221 A1 | 7/2014 | Frank | |
| 2014/0244277 A1 | 8/2014 | Krishna Rao | |
| 2014/0249860 A1 | 9/2014 | Rynchek | |
| 2014/0253467 A1 | 9/2014 | Hicks | |
| 2014/0304005 A1* | 10/2014 | Hughes | G06F 3/041 705/3 |
| 2015/0058013 A1 | 2/2015 | Pakhomov | |
| 2015/0164436 A1* | 6/2015 | Maron | A61B 5/7278 340/540 |
| 2015/0178457 A1* | 6/2015 | Grimley | G06F 3/04817 705/3 |
| 2015/0228277 A1 | 8/2015 | Anhari | |
| 2015/0257681 A1 | 9/2015 | Shuster | |
| 2015/0258892 A1 | 9/2015 | Wu | |
| 2015/0314681 A1 | 11/2015 | Riley, Sr. | |
| 2015/0363657 A1 | 12/2015 | Shigemura | |
| 2015/0379200 A1* | 12/2015 | Gifford | G16H 10/60 705/3 |
| 2016/0004820 A1* | 1/2016 | Moore | H04W 4/21 705/3 |
| 2016/0012196 A1* | 1/2016 | Mark | G06Q 10/00 705/2 |
| 2016/0080403 A1 | 3/2016 | Cunningham | |
| 2016/0297359 A1 | 10/2016 | Kirsch et al. | |
| 2016/0342741 A1* | 11/2016 | Chin | G06Q 50/22 |
| 2017/0007167 A1 | 1/2017 | Kostic | |
| 2017/0060997 A1 | 3/2017 | Lee | |
| 2017/0190251 A1 | 7/2017 | Wu | |
| 2017/0195637 A1 | 7/2017 | Kusens | |
| 2017/0200449 A1 | 7/2017 | Penilla et al. | |
| 2017/0235888 A1* | 8/2017 | Rahman | G06F 17/2785 705/3 |
| 2017/0359551 A1 | 12/2017 | Shaw | |
| 2018/0027006 A1* | 1/2018 | Zimmermann | H04L 63/0245 726/11 |
| 2018/0032997 A1* | 2/2018 | Gordon | G06Q 20/3224 |
| 2018/0060899 A1* | 3/2018 | Das | G06Q 30/0237 |
| 2018/0090155 A1 | 3/2018 | Moriya | |
| 2018/0144763 A1* | 5/2018 | Khaleghi | G10L 15/26 |
| 2018/0193652 A1 | 7/2018 | Srivastava | |
| 2018/0200142 A1* | 7/2018 | Freeman | G16H 40/20 |
| 2018/0267700 A1* | 9/2018 | Kaditz | G06F 3/04847 |
| 2018/0285542 A1 | 10/2018 | Xiao | |
| 2019/0006040 A1 | 1/2019 | Fleming | |
| 2019/0035132 A1* | 1/2019 | Dirksen | G10L 19/038 |
| 2019/0208354 A1* | 7/2019 | Raduchel | H04W 4/02 |

OTHER PUBLICATIONS

Mullin, "Rewriting Life—Voice Analysis Tech Could Diagnose Disease," 3 htttgs://www.technologyreview.com/s/603200/voice-analysis-tech-could-diagnose-disease/; Jan. 19, 2017; 9 pages.

Nield, "Scientists Can Now Diagnose Depression Just by Listening to Your Voice," IEEE Transactions 4 on Affective Computing; Science Alert, httgs://www.sciencealert.com/this-comguter-grogram-can-tellwhen-someone-s-deoressed-bv-their-soeeach-oatterns; Jul. 11, 2016; 4 pages.

Scherer et al., "Investigating Voice Quality as a Speaker-Independent Indicator of Depression and 5 PTSD", University of Southern California, Institute for Creative Technologies; 5 pages; Los Angeles, California, 2013.

PCT International Search Report and Written Opinion, regarding International Application No. PCT/US2019/019438, dated Jun. 14, 2019, 19 pages.

* cited by examiner

YOUR NOTEBOOK

SLECTION THE CONDITION IS THE NOTEBOOK IS FOR?

AUTISTIC SPECTRUM DISORDER

DEVELOPMENT DISORDER

LEARNING DISORDER

EMOTIONAL OR PSYCHIATRIC DISORDER

AGING

LIFE ALTERING ILLNESS (CANCER, PARKINSON'S, ALS, ETC..)

OTHER

FIG. 4A

WHO IS THE PATIENT

PATIENT:

Name:

Address:

Male/Female:

Gender Identification

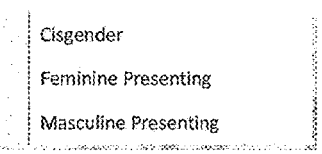
- Cisgender
- Feminine Presenting
- Masculine Presenting

D.O.B.:

Diagnosis:

If the patient is not the one using the Notebook, then who is?

Relationship to patient?

Who lives with the patient?

Who attends to the patient on a daily basis?

Is there support family members or staff that assist with the patient? ☑

FIG. 4B

*MY HEALTH TIMELINE*

The information that begins to form this *Health Timeline* is basic biographical information. It may take time to fill this time line in because it will ask questions that may take a bit of research on your part.

For example it took research to understand that there was a correlation between Shingles and Chicken Pox. We don't always know what is connected at the moment but taking the time to provide answers to questions may help in the big picture.

FIG. 4C

*AUTISTIC SPECTRUM DISORDERS*

What is the patient's relationship with person using the Notebook?

Self, Parent, Spouse, Family Member (specify), Other (specify)

[                                              ]

Diagnosis: [                    ]

Age at first diagnosis? [      ]

Are there other family members with this diagnosis? [              ]

If yes, who family member(s): [        ] [        ] [        ] [        ]

Are there other family members with another developmental or psychological diagnosis?

[        ]

If yes, who is the family member and what is the diagnosis?

[      ] [      ] [      ] [      ]

Who does the patient live with? [      ] [      ] [      ]

Who takes the patient to their appointments? [      ] [      ]

Who is the holder of information on the patient? [      ]

Has an IEP (Individual Educational Plan) been done on this patient? [    ]

If yes, when and where? [        ] [              ]

Is there an educational specialist that works with this patient? [    ]

If yes, who? [        ]

Is the patient part of any educational program or study? [    ]

If yes, what program or study? [              ]

FIG. 4D

DEVLOPMENTAL DISORDERS
LEARNING DISORDERS

What is the diagnosis?

When was the diagnosis given?

Who is the primary treatment professional for this patient?

Are there any other family members with this or similar diagnosis?

Has an IEP (Individual Education Plan) been done on this patient?

If yes, when and where?

What is the patients learning environment?

FIG. 4E

*EMOTIONAL OR PSYCHIATRIC DISORDERS*

What is the diagnosis? ⬜

What was the age at diagnosis? ⬜

Are there any other diagnosis, please list: ⬜ ⬜ ⬜

Are there any chemical dependency issues? ⬜

If the patient is dually diagnosed, has the patient ever been in dual diagnosis or addiction treatment? ⬜

If yes, provide details. ⬜

Has the patient ever been hospitalized, either voluntarily or against their will? ⬜

Are there any other family members with this diagnosis?

If yes, provide details. ⬜

Is the patient in treatment with Emotional Health Professionals? ⬜

Is the patient taking medication? ⬜

If yes, what medication? ⬜ ⬜ ⬜

*AGING*

One of the most important things that older adults can do to take care of themselves is to have one primary treatment professional who holds all information.

As we age we begin to visit specialists and each specialist by definition take care of one particular part of our health. Tests are often ordered and medication is often prescribed.

Sometime tests overlap and sometime medication interacts.

When you have one primary treatment professional as the holder of the information then the above two are less likely to happen.

And The Notebook will keep everyone in the loop.

Who is the specialist? [          ]

What is the reason for the visit to the specialist? [          ]

Will tests be conducted? [          ]

If yes, the test results should go to the referring primary physician for review.

Is medication being prescribed, and if so, which medications? [    ] [    ] [    ]

If medication is being prescribed who is following up? [          ]

The referring primary physician must be alerted to any prescription medication being given.

The specialist contact information and other details will be added to the contact database and other appropriate sections of the Notebook.

The primary physician and/or team leader will be alerted to follow-up if recommended or prescribed treatments, visits, follow-ups, or tests, are not performed.

FIG. 4G

LIFE ALTERING ILLNESS

What is the patient's relationship with the person using the Notebook?

Self, Parent, Spouse, family member (specify), other (specify)

What is the diagnosis?

When was the diagnosis given?

Who gave the diagnosis?

Is there a treatment plan that has been established?

Who monitors the treatment plan?

How does the patient get to and from appointments?

Does someone go to the appointments with the patient?

FIG. 4H

AT YOUR APPOINTMENT

Use the record function, or dictate function, on your phone, tablet, or other device to record the meeting with the treatment professional.

With this record/dictate function the content of the meeting will be recorded so that you will not need to write down and remember every detail of what the treatment professional said, thereby reducing stress. This will allow you to be more present during the appointment which leads to getting more out of each professional.

Typically, the face-to-face time that you have with the treatment professional is limited. As a result of the limited time and the inherent stress of the appointmentm it can be very difficult to take in the information provided and to follow up and recommendation details.

It is strongly recommended that you have a list of questions for the medical professional prepared and entered into the Notebook prior to your appointment. When you do not go in with a list of questions or areas of concerns, you are likely to forget to ask such questions, and you will leave feeling remorse that you did not remember to ask about concerns that came up between appointments.

The Content Dictation:
The appointment with the treatment professional will be recorded.
When the meeting is organized into The Notebook the items that will be highlighted may include one or more of the following:
Professional Recommendations; if a test, or medication, or intervention is recommended by the treatment professional then it will appear as a Reminder in the notes and will be cued until notation is made that the recommendation is implemented.
Specifics on the recommendation are highlighted.
When the word "problem", "worry", "concern" or any derivative is used it will be picked up and will appear in the Needs column.

FIG. 4I

The List

The list may used when at appointment with treating professional

You may dictate the list, and the Notebook with convert the dictated list to text.

You may also handwrite or type the list into the Notebook.

When generating the list, indicate the treatment professionals name and then the area of concern that you wish to address.

The Notebook will generate a "Reminder" in the Calendar that will display the list on the day of the appointment.

A cue will bring up the item of concern that will allow you to indicate if the items is resolved or still pending.

The Notebook will indicate the recommended resolution and the method of resolution will show up in the form of a "Reminder".

RECORD

FIG. 4J

*The Referral*

Who provided the referral? [_____]

When was the referral provided? [_____]

What is the name of the referral? [_____]

What is the referral's specialty? [_____]

What was the goal of the referral? [_____]

Is there a report or test to be completed or conducted? [_____]

The professional that is to be seen in referral will be added to the contact list.

And the accompanying sections pertinent to the appointment, etc. will be augmented.

FIG. 4K

CONTACTS

Provider Name:
    Address:
    Phone:
    Email:
    Fax:
    Assistant/Associate in Office:
    Specialty:

CONTACTS PART 2

Who referred to this provider?:
Dates of visit:

FIG. 4L

*OFFICE VISITS*

Name of Provider:

Date of Visit:

Reason for Visit:

Visit Notes:

Recommendations from Visit:

Referral Given at Visit:

Follow up appointment needed:

Impressions of visit:

FIG. 4M

*THE WALL*

The purpose of this section is to share and receive information from those in similar situations.

The question that those writing on The Wall need to ask themselves is;

What I found to be useful/helpful?

What I tried and did not work?

SEARCH

TAGS

*TREATMENT PLAN*

Who is the person who is in charge of monitoring the treatment plan?

Physician?

Family Member?

Treatment Professional?

Is there a prescribed follow-up schedule?

If yes, provide follow-up schedule information:

When there is a prescribed follow-up interval or time table the patient, care giver/ significant other, team leader etc. will be alerted to follow-up with the treatment plan.

If the followed-up has not occurred in the prescribed time frame then the treatment professional attached to the follow-up will be alerted to check in with the patient, et al.

FIG. 40

Medications and Procedures

Medications:

- What is the name of medication?

- Who prescribed?

- What is the medication supposed to do?

- When was this prescription first ordered?

- What is the protocol (how is medication taken, how often, etc) with the medication?

- Who is following up on the efficacy/effectiveness of the medication?

- According to the prescriber, how long will it take for you to determine if the medication is having the desired results?

- What are the side effects?

- Are there any medications or foods that must be avoided while taking this medication?

- What is the follow up plan on this medication

Medical Procedures

What medical procedures have been done?

- Date:

- Procedure:

- Who ordered Procedure?

- Where was Procedure done?

Whenever possible you should hold a copy of the procedure results.

- Do you have a copy of the procedure results?

- If no, who has the procedure results?

FIG. 4P

CLINICAL OR THERAPEUTIC TREATMENT

Is the patient seeing a therapist, psychiatrist or psychologist?

If yes, who?

How often?

Is any other family member seeing one of the above?

If yes, provide detailed information.

Has any psychological testing been done?

If yes, provide detailed testing information

FIG. 4Q

DIARY/CHRONOLOGY

DATE  EVENT

[ ]  [ ]  (More)

[ ]  [ ]  (More)

[ ]  [ ]  (More)

[ ]  [ ]  (More)

FIG. 4R

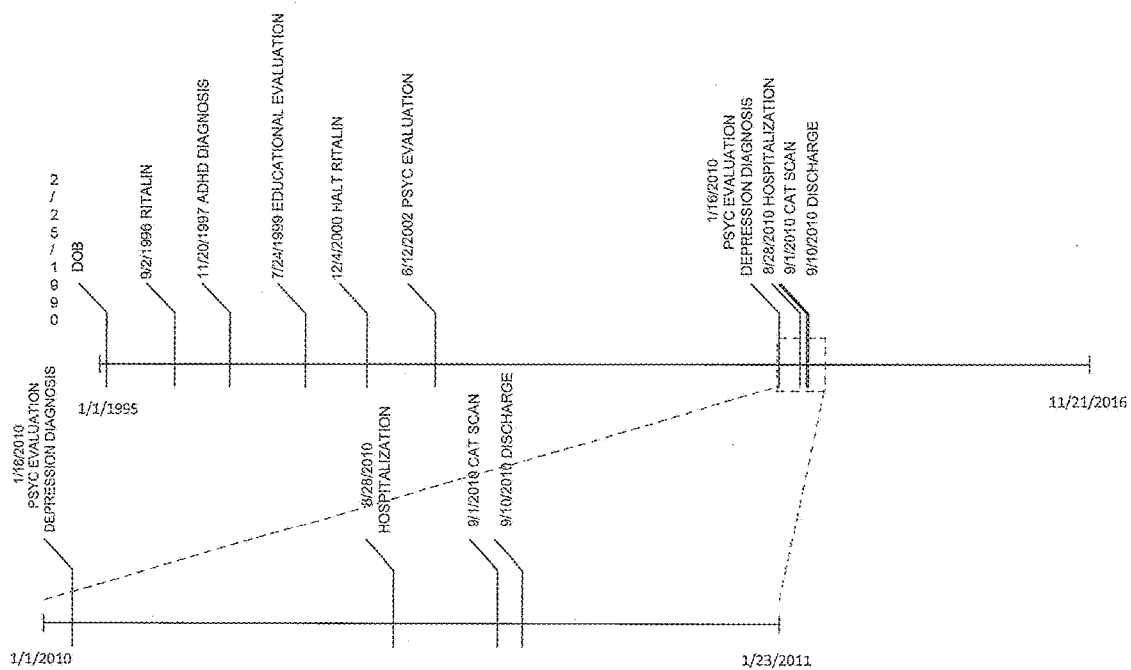
FIG. 4S1

*MASTER COMBINED*

The *Master Combined* meshes the *Biographical, Medical, Clinical, Therapeutic* and *Diary* into a merged timeline

FIG. 4S2

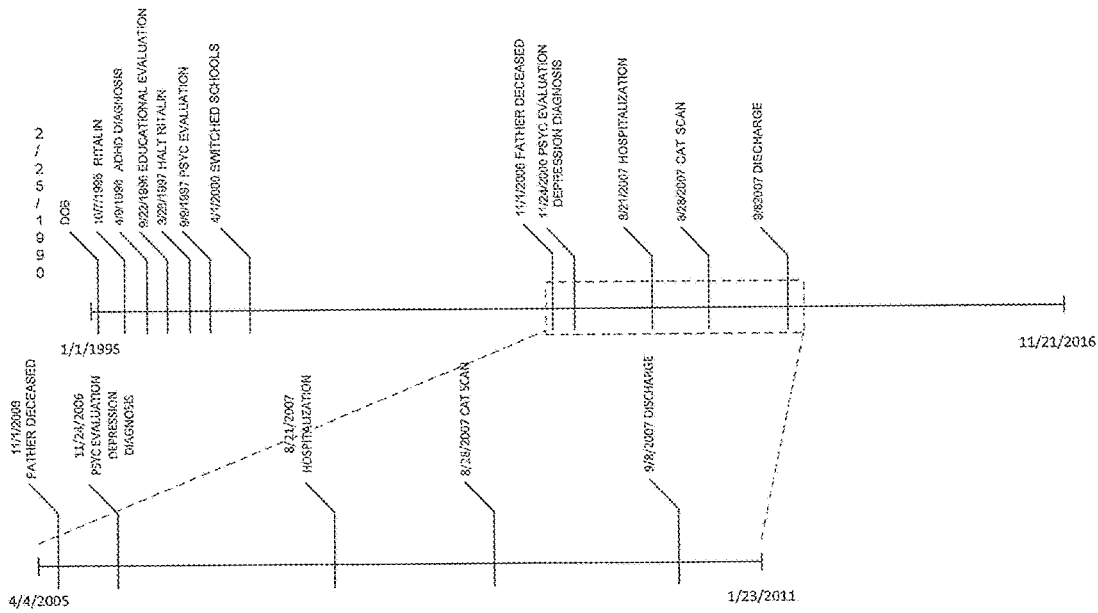
FIG. 4S3

CHECKING IN

Are you the:
-Patient or
-Significant Other/Care Giver/Family Member

FIG. 4T

CHECKING IN

If the patient is performing the check-in the patient is to answer the following:

- Do I know how I feel?
- I would describe how I feel in this way:
- The things that are working are;
- The things that are not working are;
- What I would like you to know;
- What nobody else knows is;
- My body feels;

If the someone other than the patient is performing the check-in, please answer the following:

- In my estimation things are going;
- I am most concerned about;
- I am feeling;
- What I do not feel the patient is telling you is;
- I really need help with;

Patient updates and concerns 

FIG. 4U

WHAT IS NEW

You can opt to receive new information about your area of concern.

Receive new information?

What subjects are you interested in?

*BIOGRAPHICAL INFORMATION*

This is really the story of your life.

Ethnicity:

Where are your family's roots (e.g., where were your parents born)?

Were there any special problems in your family of origin?

Were there any health problems or illness in your family of origin?

Where we you born?
City & State

Do you have siblings?
If yes, how many brothers, how many sisters, and what are there ages?

Where there any deaths in your family that were unexplained?

Please list the places (city and state) that you have lived since your birth?

FIG. 4W

*MONEY MATTERS*

This is the "who pays for what" section.

In this section you will have the option of including insurance information that will help you will the submission of claims to your insurance company as well as the keeping track of what your insurance has paid and what needs follow-up or additional information.

Do you have insurance?

If yes, provide insurance information.

Do you want to use The Notebook for keeping track of insurance billing and matters?

If yes, please provide information regarding claims.

Do you have disability coverage?

Do you have Long Term Disability Coverage (LTD)?

If yes, provide information.

Do you want to use The Notebook for keeping track of your LTD?

If yes, provide information regarding claims.

Do you have Supplemental Security Income (SSI)?

If yes, provide information

Do you want to use The Notebook for keeping track of your SSI?

If yes, provide information

Do you have Social Security Disability Insurance (SSDI)?

If yes, provide information

Do you want to use The Notebook for keeping track of your SSDI?

If yes, provide information
There is a grid for helping to keep track of payment made to treatment providers.

When you use The Notebook to keep track of who pays what it will notate when payment is made.

FIG. 4X

RESOURCES

Diagnosis or cluster of diagnosis:

AcmeDiagnosisinformation.com
ZetaDiagnosisinformation.com

Type of Specialty or Need

BetaNeedInformation.com
SpecialtyOmega.com

Geographical Region (city, state, or zipcode)

Search

FIG. 4Y

Your Team

| | |
|---:|:---|
| Team Leader Name | ☐ |
| Team Leader Function/Specialty | ☐ |
| Team Member 1 Name | ☐ |
| Team Member 1 Function/Specialty | ☐ |
| Team Member 2 Name | ☐ |
| Team Member 2 Function/Specialty | ☐ |
| Team Member 3 Name | ☐ |
| Team Member 3 Function/Specialty | ☐ |
| Team Member 4 Name | ☐ |
| Team Member 4 Function/Specialty | ☐ |
| Team Member 5 Name | ☐ |
| Team Member 5 Function/Specialty | ☐ |
| Team Member 6 Name | ☐ |
| Team Member 6 Function/Specialty | ☐ |

FIG. 4Z

ELECTRONIC NOTEBOOK SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This document relates to systems and techniques for electronic notebooks.

Description of the Related Art

Conventional techniques for recording information include physical notebooks and simple electronic notebooks. However, such notebooks tend to be static in nature, recording manually entered information and manually selected locations and then displaying such information as entered.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

This document describes systems, processes and techniques that may be used to manage and process the recording, arrangement, text processing, word recognition, and/or review of information for or in an electronic notebook such as a patient, psychiatrist, psychologist, or other medical professional electronic notebook. For example, an electronic or digital notebook may optionally be managed by a hosted a secure, cloud based system comprised of co-located and/or geographically distributed server systems. The electronic notebook may be accessed over a network by one or more users via one or more users. For example, the users may comprise one or more medical professionals (e.g., a psychiatrist, a family physician, a neurologist, a geriatrician, a therapist, etc.), a patient, a family member of the patient, a caretaker, etc. The electronic notebook may enable two or more users to collaborate over a network with respect to a patient's data and care. Optionally, a user of the electronic notebook may issue an invitation to one or more other users to collaborate.

BRIEF DESCRIPTION OF THE DRAWINGS

Embodiments will now be described with reference to the drawings summarized below. These drawings and the associated description are provided to illustrate example aspects of the disclosure, and not to limit the scope of the invention.

DETAILED DESCRIPTION

Figure 1:
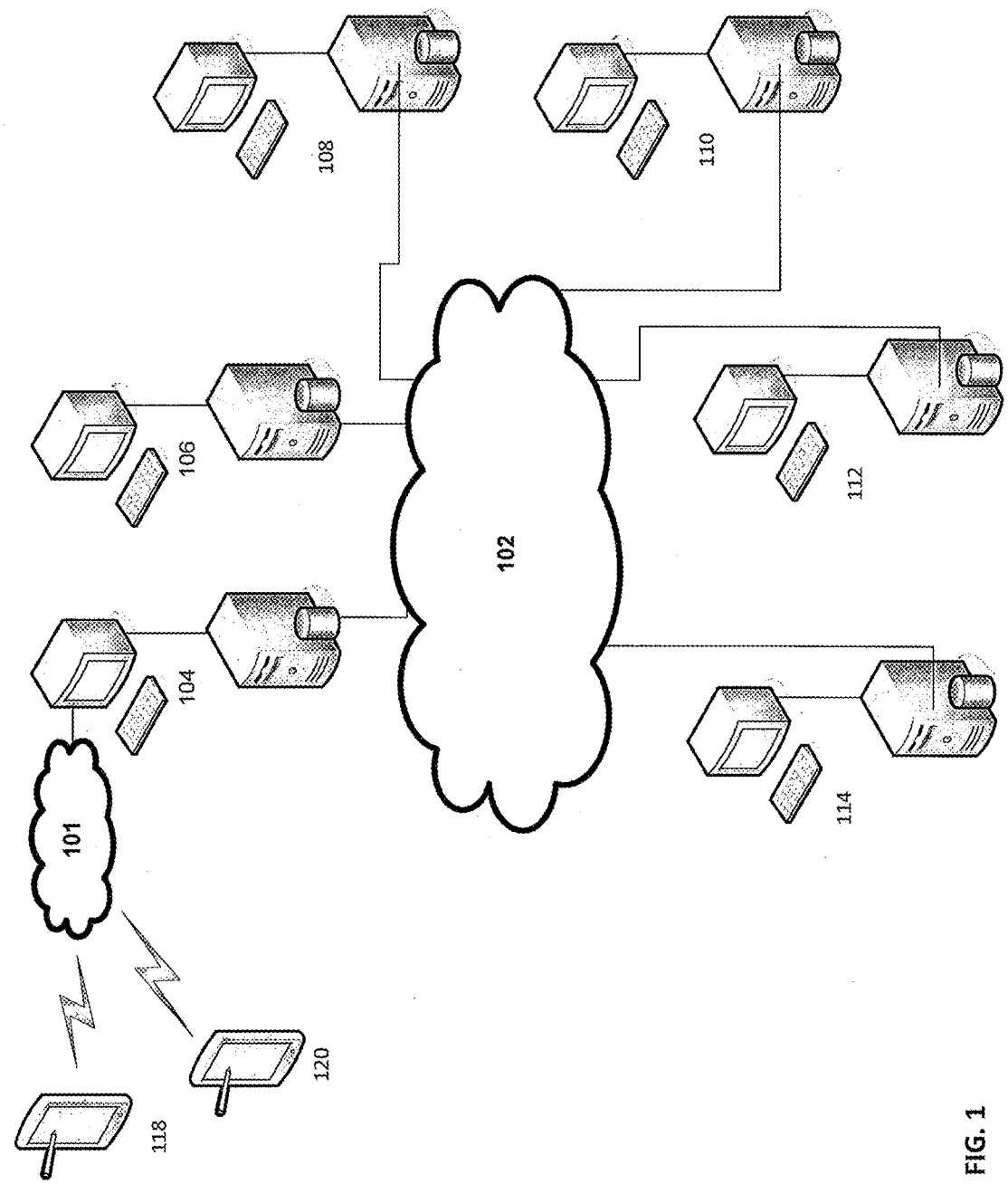
FIG. 1 illustrates an example architecture.

This document describes systems, processes and techniques that may be used to manage and process the recording, arrangement, text processing, word recognition, and/or review of, information in an electronic notebook such as an electronic psychiatrist, psychologist, or other medical professional notebook. For example, a notebook may optionally be managed by a hosted a secure, cloud based system comprised of co-located and/or geographically distributed server systems. The electronic notebook may be accessed over a network by one or more users via one or more user terminals (e.g., via a desktop computer, laptop computer, tablet, smart phone, networked television, network connected wearable device). By way of illustration the electronic notebook may be accessed as a web document via a browser and/or via a dedicated application (sometimes referred to herein as an "app") installed and hosted on a user device. Optionally, some or all of the information processing described herein may be performed via a system remote from the user terminal (e.g., by the cloud system), or optionally some or all of the information processing described herein may be performed by the user terminal. Optionally, some of the information processing described herein may be performed via a system remote from the user terminal (e.g., the cloud system), and some of the information processing described herein may be performed by the user terminal. The notebook may include multiple sections, as discussed elsewhere herein. Optionally, the various electronic notebook sections may be organized using visual tabs.

Information between a user terminal and the remote system may be synchronized periodically and/or in response to an event (e.g., a detection of a change of data or receipt new data). By way of example, as will be discussed in greater detail herein, a system (e.g., the cloud system or a user device hosting an electronic notebook application) may generate, using information recorded or accessed via the electronic notebook a health timeline for a patient. The health timeline may be updated and the updates may be continuously or periodically synchronized.

The following example relates an electronic medical information notebook. Optionally, some or all of the information communicated between a user terminal app (e.g., an electronic notebook app) and a remote system are transmitted securely to comply with certain regulatory specifications. For example, in order to ensure confidentiality of medication information, the medical information may be handled so as to comply with the Health Insurance Portability and Accountability Act (HIPPA). For example, some or all of the information may be encrypted using an encryption key.

The data may be secured by establishing a virtual private network (VPN) which establishes an encrypted transmission path between the user terminal and remote system. Optionally, Secure Sockets Layer (SSL), a secure transfer tunnel, may be used to encrypt data in transit between the user terminal (e.g., the notebook app and/or browser) and the remote system. Optionally, some or all of the information may be stored on the user terminal and/or the remote system using file encryption. Optionally, the encryption key may be stored physically separate from the data being encrypted (e.g., on different physical servers).

Optionally, access to notebook and/or other medical information is restricted through user authentication. User authentication may be received in the form of a password and/or biometrics. For example, the user terminal may be equipped with a fingerprint scanner which may be used to compare a fingerprint of someone attempting to access the user terminal and/or the notebook information with that of an authorized user. If there is a match access may be granted to the user terminal and/or notebook information. If the fingerprints fail to match, access to the user terminal and/or notebook information may be denied. Another form of biometrics may be in the form of facial recognition. For example, the user terminal may be equipped with a camera which may be used to capture an image of someone attempting to access the user terminal and/or notebook information. Features extracted from the image may be compared to stored features of an authorized user. If there is a match, access may be granted to the user terminal and/or notebook information. If the facial features fail to match, access to the user terminal and/or notebook information may be denied. Other authentication techniques may be used, such as voice recognition, secure fobs, and the like.

Optionally, the users may comprise one or more medical professionals (e.g., a psychiatrist, a family physician, a neurologist, a geriatrician, a therapist, etc.), patients, patient family member, etc. The electronic notebook may enable two or more users to collaborate over a network. Optionally, a user of the electronic notebook may issue an invitation to one or more other users to collaborate. For example, the collaboration may relate to providing information with respect to a patient (e.g., past or recommended future treatments, changes in the patient's life style, etc.). The invitation may be transmitted from the user's terminal directly to the invitee's terminal, or the invitation may be routed through the remote system to the invitee's terminal. The invitation may be provided to the invitee via a pop-up invitation displayed on the invitee's terminal (e.g., by the notebook app), via an SMS/MMS message, via an email message, via a notebook interface presented via a browser, etc.

A user (who may be patient, a medical professional, a family member, a caretaker, etc.) may utilize the electronic notebook to record information regarding a patient/client (e.g., a patient with a mental or physical illness, a patient with a physical or cognitive disability, a patient with a drug addiction issue, a patient with aging-related issues, etc.). The notebook may be used to record, process, and reproduce textual information, audio recordings, video recordings (which may include an associated audio recording track), photographs, medical diagnoses, x-rays, MRI scans, CAT scans, PET scans, medical test reports, medical treatment information, and/or other information. For example, textual information may include questions asked by a medical professional of a patient and/or patient's family members, and responses to such questions. Optionally, a given item of information recorded in the notebook may be stored in association with metadata, such some or all of the following an identifier (e.g., name or user ID) associated with the user that recorded the information, an identifier indicating the user function (e.g., psychiatrist, patient, parent of the patient, child of the patient, etc.), geo-location information indicating the physical location of the user when the user entered in the information (e.g., GPS location information received from the user terminal, such as a mobile phone), etc.

By way of example, the electronic notebook may be utilized to record which medical professional a patient first encountered when admitted to an emergency room, other medical professionals the patient was treated by in the emergency room, who performed which tests (e.g., x-rays, MRI, other scans, blood tests, etc.). By way of further example, the electronic notebook may be used to list potential diagnoses, and to indicate when a given listed diagnosis has been determined to be no longer a potential diagnoses.

The notebook may also be used to search for and/or display specialists of a specified type that are in the geographic area of the patient (e.g., within a specified region, city, zip code, a specific number of miles from the patient's residence and/or from the device hosting the notebook, etc.). For example, a search for specialists of a specified type that are in the geographic area of the patient may be executed by a search engine which will return a list of names that satisfy the search criteria. The specialist's name may be presented by the notebook app (or a browser) in the form of a link or in association with a link, wherein if the user clicks on the link, the notebook will access and display additional information regarding the specialist, such as the schools attended, the hospitals where the specialist interned, the hospitals where the specialist had a fellowship, the hospitals that the specialist has admission privileges for, rating from one or more rating sources, etc.

The electronic medical information notebook may be configured to make it easy for a patient or patient caretaker to access and understand the medical information, and to enter information, as well as appointments, records, and to do lists. As will be discussed, the electronic notebook may include user interfaces configured to receive background and biographical information for a patient, the ability to record verbal discussions at an appointment, the ability to convert voice-to-text, the ability to generate lists of questions that are to be asked at an appointment, the ability to transmit the list of questions to one or more recipients prior to the appointment, the ability to record referral information, the ability to receive and record contact information, the ability to record office visit notes, the ability to share information from the notebook with others, the ability to record treatment plan information, the ability to record medication and prescription information, the ability to record medical procedure information, the ability to record a diary/chronology of appointments, interventions, testing, etc., the ability to combine the diary with collected biographical, medical and clinical information, the ability to communicate with medical professionals (e.g., for the purposes of providing check-in information via video conferencing or messaging, text chats, VoIP, or otherwise), the ability to receive updates relevant to a user's area of concern, the ability to record, track, and analyze medical insurance related matters, the ability to search for and access resources by diagnosis, the ability to calendar events, such as medical appointments.

FIG. 1 illustrates an example architecture. A notebook management system 104 (which may be a cloud based system comprising one or more servers that are co-located and/or that are geographically dispersed) may host one or more applications that when executed cause a variety of the processes (e.g., the backend processes) described herein to execute. Optionally, the cloud system may include one or more Apache Hadoop clusters, optionally including a Hadoop distributed file system (HDFS) and a Hadoop MapReduce parallel processing framework. The system 104 may be configured to process and store large amounts of data that would not be effectively by conventional system. The system 104 may be configured to process and store large amounts of structured data, unstructured data, and/or semi-structured data. The data may relate to the patient-related data (including sound and/or video recordings, scans, test results, contact information, calendaring information, biographical data, patient-related team data, etc.) disclosed herein. The clusters may comprise master nodes (e.g., a name node, a job tracker, etc.), and slave nodes (e.g., data nodes, task trackers, etc.). A given data node serves data over a network using the distributed file system (e.g., HDFS) protocol. The file system may utilize a TCP/IP layer for communication. The distributed file system may store large files across multiple data node machines and may store copies of data on multiple hosts to enhance reliability and data availability.

With respect to the optional Hadoop implementation, other systems may submit tasks to the job tracker, which in turn, distributes the tasks to available task tracker nodes. Optionally, the job tracker may attempt to distribute a given task to a node in geographic proximity to the needed data. While the foregoing example refers to Hadoop clusters and related components, other distributed platforms may optionally be used in addition or instead to process and store data, such as large amounts of data including structured, unstructured, and/or semi-structured data, (e.g., distributed platforms utilizing Bashreduce, Qizmt, Spark, Disco Project, etc.).

The notebook management system 104 may communicate over one or more wired and/or wireless local and/or wide area networks (e.g., the Internet) 101 with one or more user terminals 118, 120. The user terminals 118, 120 may be wireless mobile devices, such as smart phones, tablets, laptops, wearables, or the like. The wireless mobile devices may optionally be equipped with wireless interfaces to communicate over WiFi, Bluetooth™, other local area wireless networks, other personal area networks, cellular networks, or the like. The wireless mobile devices may optionally be equipped one or more antennas connected to respective wireless interfaces. The antennas may be located within the housing of the mobile device, and or on the housing surface of the mobile device. The user terminals 118, 120 may be wired or wireless non-mobile devices, such as a desktop computer, a fixed or large networked television, a game console, or the like. The user terminals 118, 120 may include a variety of sensors (e.g., sound, image, orientation, pressure, light, acceleration, and/or other sensors) configured to detect user input and interaction with the user terminals 118, 120. The user terminals 118, 120 may include touch screens configured to display user interfaces and data and receive user input via touch. The user terminals may include physical keyboards. The user terminals 118, 120 may include one or more microphones to receive voice data and commands, and one or more speakers to play audible content. The user terminals 118, 120 may include a camera configured to capture, record, and/or stream video data (which may be stored or streamed in association with captured audio data) to other systems, such as the notebook management system 104. The user terminals 118, 120 may be associated with the various user-types discussed herein, such as patients, family members of patients, patient caretakers, medical personnel, medical facilities, or other members of a support network.

The notebook management system 104 may communicate over one or more wired and/or wireless local and/or wide area networks 102 with one or more remote servers or computing systems 106, 108, that may be associated with medical service providers, one or more medical databases 108, 110, or third party contact and calendar systems 112, 114. The network 101 and the network 102 may be the same or different networks.

Figure 2:
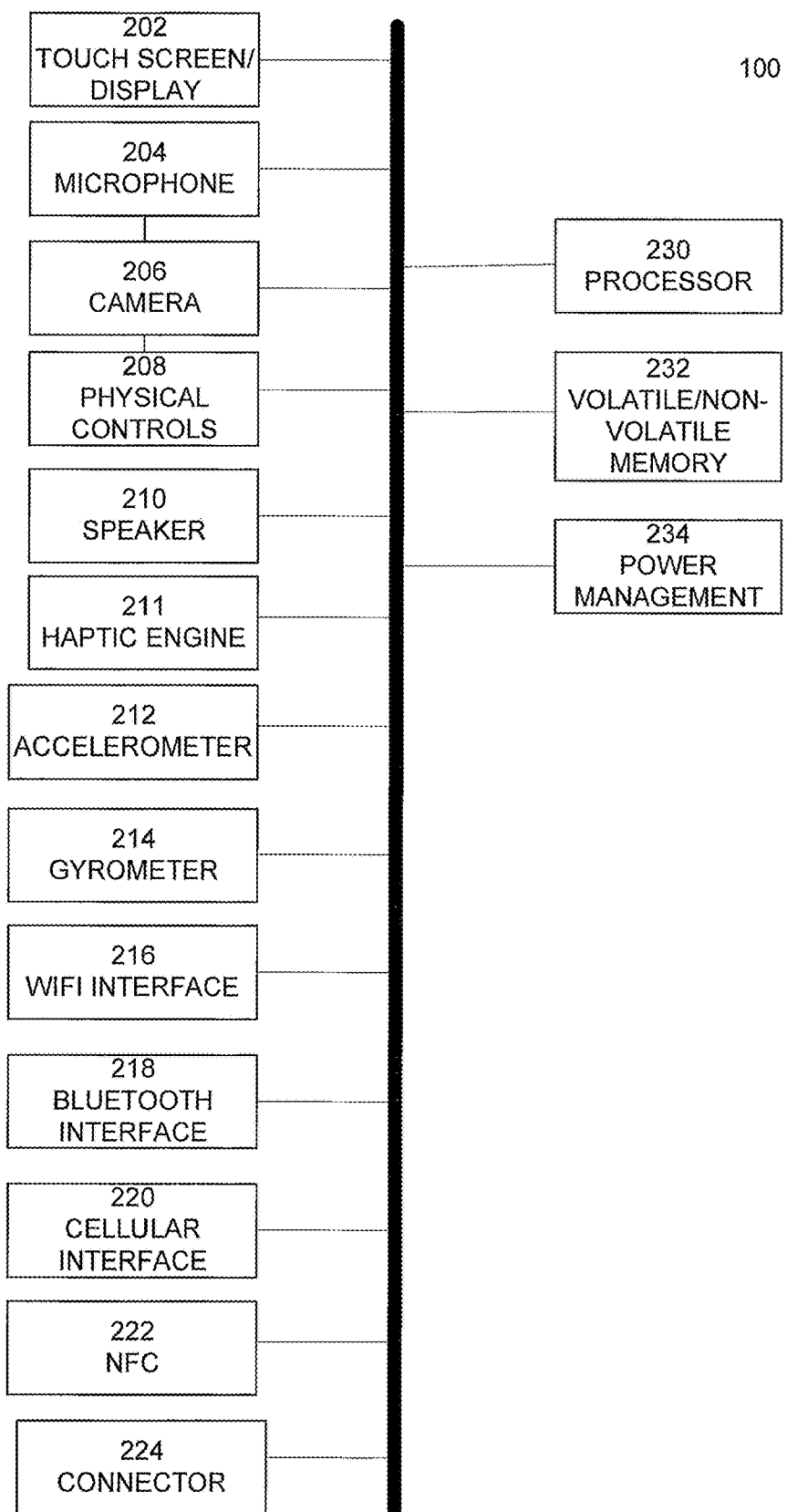
FIG. 2 illustrates an example user terminal architecture.

FIG. 2 illustrates an example user terminal in the form of a tablet, phone, or laptop. In the example illustrated in FIG. 2, a user terminal 200 includes various user input/output devices, such as a touchscreen/display 202, a microphone 204, a camera 206, physical controls 208 (e.g., a power on/off control, a volume control, a home control, etc.), a speaker 210, and/or other user input/output devices. The user terminal 200 may optionally include a haptic engine 211 that provides kinesthetic communication to the user (e.g., via vibrations or taps, which may be used to confirm a user input or to provide a notification), an accelerometer 212 that measures acceleration in 2-3 directions, and a gyrometer (e.g., a 3-axis gyroscope) 214 that measures orientation in three axis. The user terminal 200 may be equipped with an external or integral physical keyboard, trackpad, joystick, electronic pen, and/or other input device.

The user terminal 200 may include one or more wireless and/or wired interfaces. For example, the user terminal 200 may include a WiFi interface 216, a Bluetooth interface 218, a cellular interface 220, an NFC (near field communication) interface 222, and/or one or more physical connectors 224 (e.g., a USB connector, a LIGHTING connector, and/or other connector). The user terminal 200 further comprises a processor device (e.g., a microprocessor) 230, volatile memory (e.g., RAM solid state memory) and non-volatile memory (e.g., FLASH memory), and a power management device 234.

The electronic notebook application may be provided or accessed in the form of any application obtained/downloaded by the user terminal 200 via a third party application store and/or via the notebook management system 104. As described herein, the electronic notebook user interfaces may include a variety of data entry fields. The fields may be populated via a keyboard, a stylus, via voice entry (provided via the microphone 204) which may be converted to text via a voice-to-text module, or via facial, limb, or figure gestures captured by the camera 206. The keyboard and/or stylus may be included with the user terminal 200. The stylus may optionally be configured with a sensor to determine stylus inclination and/or a sensor to measure the pressure being applied to the stylus by the user. The pressure and inclination information may be transmitted to the user terminal 200 (e.g., via Bluetooth or other wireless or wired protocol) and such information may be used to identify user issues as described elsewhere herein.

Figure 3:
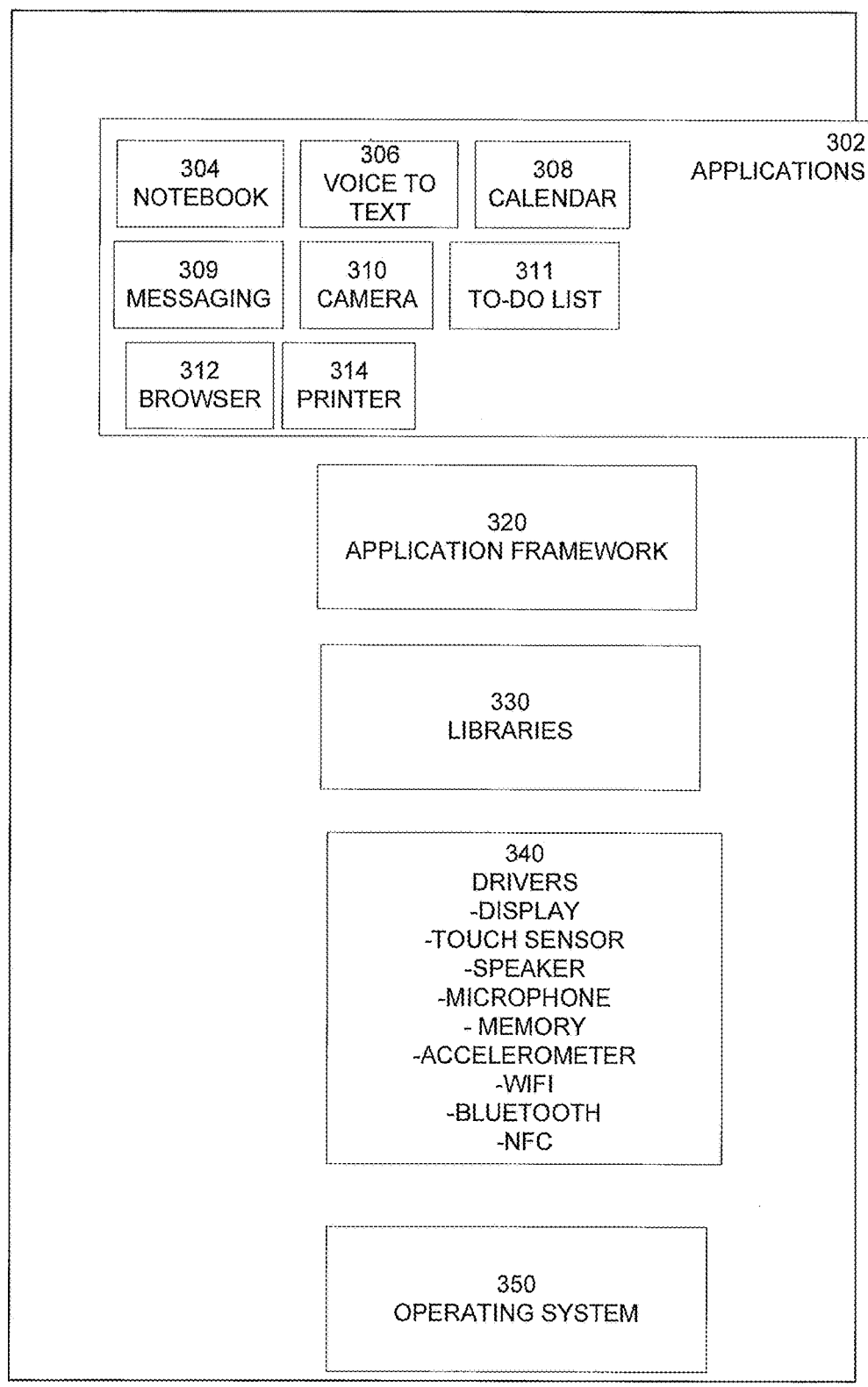
FIG. 3 illustrates an example software architecture for the example user terminal.

FIG. 3 illustrates an example, optional software architecture for a touch-enabled version of the example user terminal 200 illustrated in FIG. 2. The software architecture may include an operating system 350 (e.g., GOOGLE ANDROID, APPLE iOS, MICROSOFT WINDOWS, APPLE OS, UNIX, LINUX, etc.), drivers 340 (e.g., display, touch sensor, speaker, microphone, memory, accelerometer, WiFi, Bluetooth, NFC, etc.), libraries 330 (e.g., SSL, Webkit, SQL, etc.), an application framework 320, and applications 302. For example, the applications 302 may include a notebook application 304, a voice-text application 306, a calendar application 308, a messaging application 309, a camera application 310, a to-do list application 311, a browser application 312, a printer application 314 and/or other applications. A given application may utilize another application as part of its operation. For example, the notebook application 304 may call the voice-text application 306, the calendar application 308, the messaging application 309, the camera application 310, the to-do list application 311, the browser application 312, and/or the printer application 314. Two or more of the applications may be integrated into a single application.

The notebook application 304 may be configured to perform some or all of the functions and processes described herein.

When a user initially accesses the electronic notebook application to generate a new electronic notebook, the electronic notebook application may provide a user interface listing various medically-related conditions or categories. By way of non-limiting example, the conditions may include one or more of the following:

Autistic Spectrum Disorders
Developmental Disorders
Learning Disorders
Emotional or Psychiatric Disorders
Aging
Life altering Illness (e.g., cancer, Parkinson's, ALS)
Other FIG. 4A illustrates an example user interface via which the user can select a condition.

The application may access and/or generate an electronic notebook template customized for the selected category. For example, the notebook may include different questions and/or types of questions for different categories, and corresponding different information receiving fields. Examples of such templates will be discussed in greater detail elsewhere herein. Optionally, a free-form text field (e.g., the illustrated "Other" field) may be provided configured to receive a description of a condition that is not listed. Thus, for example, if a patient is suffering from a non-listed condition, a description of the condition, or related keywords, may be entered into the free-form field. The application may utilize natural language processing (sometimes referred to as computational linguistics) to analyze and understand the text entry. Natural language processing may comprise the utilization of machine learning that analyzes patterns in data to improve the natural language processing software's ability to understand the entry. Natural language processing may utilize sentence segmentation, part-of-speech tagging (e.g., subject, object, modification, noun, adjective, number, etc.), parsing, named entity extraction (e.g., locating and classifying elements in text into various categories such as the names of persons, organizations, locations, expressions of times, quantities, monetary values, percentages, etc.), paraphrase recognition (determining when different phrases or sentences have the same meaning), and/or co-reference resolution (finding all expressions that refer to the same entity in a text). Fuzzy logic may be used to generate or select a template that includes suitable questions and fields.

Optionally, handwritten entries provided via handwritten touch entry (e.g., via a stylus or user finger/digit) may be analyzed to identify user stress. For example, the smoothness or jaggedness of the handwritten entry may be identified (e.g., by identifying discontinuities or abrupt horizontal inputs followed immediately by abrupt vertical inputs) to infer whether the user is undergoing stress. Similarly, stylus/finger pressure and inclination information may be received (e.g., via a wireless interface), stored and analyzed to identify user stress (e.g., pressure or inclination angle above a respective threshold may indicate stress).

The electronic notebook may include fields for receiving content and/or demographic information of a patient. For example, as illustrated in FIG. 4B, the fields may include name, address, biological gender, gender identification, date of birth, and/or diagnosis. Other example fields include fields configured to receive an indication as to whether the patient is a primary user of the electronic notebook, and if not, an indication/name as to who is the primary user of the notebook, and the primary user's relationship to the patient (e.g., parent, child, sibling, caretaker, physician, etc.). Still other example fields may include a field to receive an identification as to who is living with the patient and their relationship to the patient (e.g., parent, child, sibling, caretaker, friend, etc.), an identification as to who attends to the patient on a daily or regular basis, an indication as to whether there are family members or staff that assist with the patient, etc.

As noted above, a health timeline may be generated. The health timeline may include some or all of the biographical information collected by the application. The health timeline may be utilized to help provide an overview of the patient's issues and potential relationships between such biographical information and the patient's medical issues and/or treatment. Thus, the health timeline may provide a quick overview of the patient and the patient's medical history. FIG. 4C illustrates an example health timeline data collection introduction.

Example questions and response fields presented by the application will now be discussed. Some or all of the collected data may be used to generate a health timeline.

Autistic Spectrum Disorder (see, e.g., FIG. 4D): If the selected patient category is Autistic Spectrum Disorder, the application may query the user to indicate the patient's relationship with user of the electronic notebook (e.g., the patient herself/himself, parent, spouse, child, other family member (e.g., sibling, uncle, aunt, niece, nephew, etc.), other). The application may further query the user regarding the patient's diagnosis, the patient's age when first diagnosed, whether there are family members with the same diagnosis, and if so, who are such family members (e.g., their name and/or relationship to the patient). The application may additionally query the user as to whether there are other family members with another developmental or psychological diagnosis, and if so, who are such family members (e.g., their name and/or relationship to the patient), and what is their diagnosis. The application may also query the user as to who does the patient live with, who takes the patient to medical appointments, who holds the patient's medical information (e.g., who knows what medications, the patient is on, the course of their diagnosis, the patient's treatment history, etc.). The application may query the user as to whether an IEP (Individual Educational Plan) been generated for the patient, and if so, when and by what entity. With respect to education, the application may query the user as to whether there is an educational specialist that works with this patient (and is so, who), whether the patient is participating in an educational program or study, and if so, what education program or study, and what level (e.g., what grade).

Developmental Disorders/Learning Disorder (see, e.g., FIG. 4E): If the selected patient category is Developmental Disorders/Learning Disorder, the application may query the user to indicate the patient's diagnosis, the patient's age when first diagnosed/when the diagnosis was first made, who is the primary treatment professional for the patient, are there any other family members with this or similar diagnosis, has an IEP (Individual Educational Plan) been generated for the patient, and if so, when and by what entity, and what is the patients learning environment (what education program is the user participating in).

Emotional or Psychiatric Disorder (see, e.g., FIG. 4F): If the selected patient category is Emotional or Psychiatric Disorder, the application may query the user to indicate the patient's diagnosis, the patient's age when first diagnosed/when the diagnosis was first made, does the patient have any other diagnosis, does the patient have any chemical dependency issues, has the patient been dually diagnosed (diagnosed with a mental illness and a comorbid substance abuse problem), and/or has the patient been in a dual diagnosis treatment or addiction treatment and if so provide details. The application may also ask if the patient has ever been hospitalized, either voluntarily or involuntarily, if any of the patient's family members received this diagnosis, and if so that details be provided. The application may additionally ask if the patient is currently in treatment with emotional health professionals, whether the patient taking medication, and if so, what medication.

Aging (see, e.g., FIG. 4G): If the selected patient category is aging, the application may query the user to indicate who is the specialist currently treating/seeing the patient, what is the reason for the visit to the specialist, whether any tests will be conducted by the specialist, and if so, the test types that will be conducted (where the test results will be forwarded to the referring primary physician for review). The application may also ask the user to indicate whether medication being prescribed is being prescribed for the patient, and if so, the types of medication and who will be following up with the patient to ensure that the patient is taking the medication, and the effect of the medication on the patient. The application may automatically notify the patient's referring primary physician and/or team leader (as discussed elsewhere herein) in response to detecting that the user has indicated that the patient has been newly prescribed medication. The application may also query the user to enter contact information (name, phone number, email, address, etc.) and specialty of any medical specialist the patient is seeing. As described elsewhere herein, such information may be automatically added to contact data store associated with the application.

Optionally, if the user fails to enter information in response to a given query, the application will automatically notify the patient's primary physician and/or team leader of such failure and may prompt the primary physician (e.g., via an email, text message, phone call, alert within an electronic notebook interface, or otherwise) to follow-up.

Life Altering Illness (see, e.g., FIG. 4H): If the selected patient category is life altering illness, the application may query the user to indicate the patient's relationship with the user of the electronic notebook (e.g., the patient herself/himself, parent, spouse, child, other family member (e.g., sibling, uncle, aunt, niece, nephew, etc.), other). The application may also query the user to indicate the patient's diagnosis, when the diagnosis was given, who gave the diagnosis, has a treatment plan been established, who monitors the treatment plan, how does the patient get to and from appointments (e.g., does the patient drive herself, does a family member, friend, caretaker drive the patient, does the patient take a car service, etc.), and who (if anyone) accompanies the patient to doctor appointments.

The electronic notebook may optionally include instructions with respect to voice recording appointments and regarding preparing questions for the appointment (see, e.g., FIG. 4I).

The electronic notebook may optionally include fields of user and/or patient questions for the medical service provider (see, e.g., FIG. 4J). Thus, such questions may be entered prior to the appointment, avoiding reliance on fallible memory with respect to questions or areas of concerns.

The electronic notebook may include a record control, which when activated, enables video and/or audio of a given appointment to be recorded by the device hosting or accessing the application (see, e.g., FIG. 4J). The recorded content of the appointment enables the user, patient, and/or other medical professionals to later review the recorded appointment without requiring that the user, patient, and/or other medical professional manually write or type in notes during the appointment. The recording of an appointment will reduce user and/or patient stress during the appointment as there will be no need to manually take notes. For example, because the recorded appointment may include information on new or existing treatment modes (e.g., medication, exercise, physical therapy, et.), the electronic notebook can generate and/or provide user interfaces textually providing such information, and may further generate and/or provide follow-up user interfaces that can be used to receive and record follow-up information indicating whether the patient is taking the medication, following other instructions provided by the doctor/specialist, the patient's physical condition and health, etc.

The spoken voice captured via the recording may be converted to text using a voice-to-text module. The voice-to-text module may perform the conversion using one or more of pattern matching, (where a spoken word is recognized in its entirety), pattern and feature analysis (where a spoken word is broken into bits and recognized from key features, such as the vowels it contains), language modeling and statistical analysis (in which a knowledge of grammar and the probability of certain words or sounds following on from one another is used to speed up recognition and improve accuracy), and/or neural networks (trainable brain-like computer models that can reliably recognize patterns, such as word sounds, after training).

A characterization module (which may be included in the app and/or the remote system) may be utilized to recognize certain types of content in the recorded content (e.g., in the voice recording or the text file generated by the voice-to-text module). For example, the characterization module may identify certain keywords in a given phrase, sentence or series of sentences that correspond to certain subject matter. The corresponding identified subject matter may then be selected and inserted into a corresponding field/section in the electronic notebook for convenient and organized viewing by a user. Optionally, the complete speech-to-text file for a given recording may be inserted/accessible from a calendar, where the calendar includes a listing of past and future appointments, an indication as to whether there are one or more appointment recordings, and any associated other files (e.g., test reports (e.g., drug tests, blood tests, psychiatric reports, orthopedic reports, etc.), prescriptions, imaging reports (e.g., x-ray, MRI, CAT scan, etc.). An example subject matter may include professional recommendations, and example subset subject matter of professional recommendations may include recommended tests, medications, interventions, etc. Thus, for example, if the characterization module identifies certain words or phrases that are typically associated with professional recommendations, such as "recommend" (or variations thereof, such as "recommended" or "recommends"), "prescribe" (or variations thereof, such as prescription), "dose" (or variations thereof, such as "dosage"), "refer" (or variations thereof, such as "referral"), "test" (or variations thereof, such as "tests", or equivalents, such as "exams", etc.), inspect (or variations thereof, such as "self-inspect"), "avoid," "take", "inject", etc., associated sentences or phrases may be categorized as recommendations. Another example subject matter may include patient concerns. Thus, for example, if the characterization module identifies certain words or phrases that are typically associated with patient concerns, such as "problem," "worry", "concern," "anxiety," "nervous," "agitated," "uneasy", or derivatives or equivalents, associated sentences or phrases may be categorized as concerns.

Another example subject matter may include patient history. Thus, for example, if the characterization module identifies certain words or phrases that are typically associated with patient history, such as "age at first diagnosis", "other family members with the same diagnosis," "other diagnosis," "other family members with another developmental or psychological diagnosis", "the patient has been hospitalized," "taking medication," "been prescribed," "in treatment," other patient history questions or information, discussed herein, etc.," derivatives or equivalents, associated sentences or phrases may be categorized as patient history. As similarly discussed above with respect to text entries, natural language processing may be utilized to analyze and understand the text file generated by the voice-to-text module.

If a professional recommendation is identified (e.g., a test, or medication, or intervention), it may be automatically added to a to-do list/reminder. The to-do list may be accessed via a menu entry available on some or all pages of the virtual notebook. The to-do list may optionally be presented each time a user opens the app. Once the recommendation has been implemented (e.g., the test has been performed, the patient has started taking the medication, etc.), the patient, caretaker, or medical professional, can mark the to-do item as completed/implemented. Optionally, items marked as completed/implemented may be moved from a viewable active to-do list to a completed/implemented to-do list.

Optionally, the virtual notebook may include an appointment list function. The list may enable a user (e.g., a patient or patient caretaker) to generate a list of questions to ask a medical professional at an upcoming appointment. For example, the user can enter a name of the medical professional, the medical professional specialty, the appointment date. Optionally, the user can send the list to the medical professional prior to the appointment so that the medical questions can be prepared to answer the questions. Optionally, the application will automatically issue a reminder (e.g., via a pop-up alert, an SMS/MMS message, an email message, etc.) to the user a certain period of time (e.g., a certain number of days) prior to the appointment to send the list to the medical professional. The list may be entered via a keyboard, a stylus, or via voice entry which may be converted to text via the voice-to-text module. Optionally, on the day/time of the appointment, the application may pop-up the list to ensure the user does not forget to ask the medical questions. The medical professional's responses can be recorded, converted to text, and entered in the notebook underneath or otherwise in association with the corresponding questions. The response is determined to correspond to a recommendation, it may be entered into the to-do list as similarly discussed above.

The electronic network may also include a referral user interface (see, e.g., FIG. 4K). The referral user interface may include fields used to record information regarding a medical-related referral to a medical professional. The fields may be populated via a keyboard, a stylus, or via voice entry which may be converted to text via the voice-to-text module.

The following are example referral user interface questions which are associated with corresponding user entry fields:
   Who is the referral source (e.g., the name of a medical professional that provided the referral);
   What is the name of the referral;
   What is the medical specialty of the referral;
   What is the goal of the referral;
   Is there a report or test to be completed or conducted by the referral.

Optionally, the referral contact information (e.g., phone number, email address, physical address, fax number, Skype® name, office assistant/associate, specialty) etc.) is automatically added to a contact database of the user. Optionally, other information, such as the name of the referral source, dates of appointments/visits, etc. may be recorded in the referral contact record, such as that illustrated in the contacts user interface illustrated in FIG. 4L. Optionally, the application prompts the user to approve adding the referral contact information to the contact database prior to the addition to the contact database. Optionally, other relevant electronic notebook user interfaces (e.g., corresponding calendar appointment entries) are automatically augmented with some or all of the referral's contact information.

The electronic network may also include an office visit user interface, such as the example user interface illustrated in FIG. 4M. The referral user interface may include fields used to record information regarding a medical-related office visit. The fields may be populated via a keyboard, a stylus, or via voice entry which may be converted to text via the voice-to-text module.

The following are example office user interface fields:
   Name of provider/medical professional;
   Date of office visit;
   Recommendations from office visit;
   Referrals provided at office visit;
   Follow-up appointments needed;
   Impressions of office visit.

Figure 4N:
FIGS. 4A-4Z illustrate example electronic notebook user interface.
Figure 4N:

The electronic network may also include "wall" user interface, an example of which is illustrated in FIG. 4N. The wall user interface is configured to receive from and share with others in similar situations (e.g., having similar diagnosis). The wall user interface may include the following example fields:

A search field configured to receive a user search query enabling a user to search through wall postings. For example, the user search query may be submitted to a search engine which will identify and return postings and/or links to postings that match the search query, which may be in turn displayed via the user terminal (e.g., via the notebook app or a browser interface).

A search filter user interface enabling the user to select predefined search filters to define a search or to narrow search results. For example, the filters may include one or more diagnosis or conditions (e.g., drug addiction, aging, dementia, special needs, seizure disorder, Parkinson's, cancer, hyperactivity, etc.), one or more treatments (e.g., anti-anxiety medication, chemotherapy, blood pressure medication, antiviral medications, anti-seizure medication, etc.), treatment side effects (e.g., sleeplessness, nausea, anxiety, dizziness, etc.), favorites (which will cause posts that have been marked as favorites by the user or that are posted by a posting user that has been marked as a favorite), etc.

A posting field via which the user can post information, experiences, opinions, resources, etc. There may be a field for posting what the user found helpful or useful with respect to the patient's medical issue, and there may a field for posting what the user did not helpful or useful.

A tag field via which the user can assign one or more tags to the user's post to make it easier for other users to search for and access the post. For example, the tags may include some or all of the filter terms and/or other terms.

The wall user interface may also include one or more controls, such a "favorite" control via which enables a user to indicate that certain posts or certain posting users are favorites.

FIG. 4O illustrates an example treatment plan user interface via which treatment plan information may be populated. For example, the treatment plan may include fields that are automatically populated using information recorded during an office visit and converted from voice to text, and/or the fields may be manually populated using a keyboard, stylus, or otherwise. The treatment plan user interface may include a field that specifies who is in charge of monitoring the treatment plan. For example, a physician (including name and specialty) can be specified, a family member (including name and relationship) can be specified, a treatment professional (including name and specialty) can be specified, a team leader can be specified, etc. The treatment plan may include a field which indicates whether there is a prescribed follow-up schedule, and details on any follow-up schedule. For example, the follow-up details may include follow-up dates, follow-up frequency, follow-up intervals, follow-up channel (e.g., via phone, office visit, laboratory tests, etc.), and an identification of a treatment professional designated to ensure that the follow-up occurs.

The notebook application or the remote system can track the prescribed follow-up dates, follow-up frequency, and/or follow-up intervals, and when a determination is made that it is time for a follow-up (e.g., the day of the scheduled follow-up or a specified number of days prior to the scheduled follow-up), an alert may be generated and provided to the patient, designated caregiver, significant other, specified physician, team leader, and/or other designated person to follow-up. The alert may be presented via a notification transmitted to the recipient's device (e.g., via a pop-up alert, a text message, an MMS message, an email, a calendar alert, or otherwise).

The application or remote system may detect that follow-up has not occurred (e.g., by detecting that the alert recipient and/or patient has not confirmed via a user interface that the follow-up occurred). If it is detected that the follow-up has not occurred in the prescribed time frame, then the treatment professional attached to the follow-up will be alerted to check in with the patient and/or those who were designated to perform the follow-up.

FIG. 4P illustrates an example medication and medical procedure user interface via which medication and medication procedure information may be populated. A separate medication record may be created for each medication. For example, the medication user interface may include fields which may be populated with the name of the medication, the name and specialty of the person that prescribed the medication, the goal of the medication, when a prescription for the medication was first order, the medication protocol (e.g., how is medication taken (pill, liquid, injection, etc.), how often the medication is to be taken, etc.), the name of the person that is responsible for following up on the efficacy/effectiveness of the medication, according to the prescriber, how long will it take to determine if the medication is having the desired results, the medication side effects, are there any medications or foods that are to be avoided while taking the medication, the medication follow-up plan, and/or other information.

A separate medical procedure record may be created for each medical procedure. For example, the medical procedure user interface may include fields which may be populated with the names of the medical procedures that have been performed for the patient, the date of a given procedure, the name of the person that ordered the procedure, where was the procedure performed, who performed the procedure an indication as to whether the user has a copy of the procedure results, if the user does not have a copy of the procedure results then name of the person that has a copy of the procedure results, and/or other information.

FIG. 4Q illustrates an example clinical/therapeutic treatment user interface via which clinical/therapeutic treatment information may be populated. A separate record may be created for each clinical/therapeutic treatment. For example, the medical procedure user interface may include fields which may be populated with an indication as to whether the patient is seeing a therapist, psychiatrist or psychologist, and if so, their name. The user interface may further include fields which may be populated with a treatment frequency, an indication as to whether another family member is seeing therapist, psychiatrist or psychologist and if so, the name and treatment frequency. The user interface may further include fields which may be populated with the types of psychological testing that has been performed on the patient.

FIG. 4R illustrates an example diary/chronology user interface. The diary section of the notebook may be utilized to record and view an ongoing chronology of appointments, interventions, testing, etc., and associated dates, The diary may be updated (e.g., via voice entry, a keyboard, stylus, or using information recorded via another section of the notebook) with each new appointment, intervention, test, etc. Optionally, the diary will sequentially present dates on which an event occurred, and brief description of the event (e.g., "appointment with neurologist", "prescription of Felodipine to control blood pressure," "MRI scan", etc.). Optionally, an additional information control (e.g., a "more" control) may be provided which when activated by a user will cause additional information regarding the event to be accessed and displayed. For example, the additional information may be accessed from another notebook section. By way of illustration, the information may be accessed from the office visit section, the treatment plan section, the medication section, the clinical/therapeutic treatment section, and/or other section. There may be separate diaries for different on-going health concerns.

FIG. 4S1 illustrates an example health timeline generated by the system using collected data described herein. The generated health timeline may begin at a certain point in time, such as a significant biological date (e.g. date of birth of the patient), and may indicate, in chronological order, the dates each diagnosis was made and the date of each medical intervention/treatment. Optionally, the health timeline may be updated in real time in response to the receipt of new or updated diagnosis and/or treatment data. Optionally, new or updated information may be emphasized (e.g., by color, font, icon, etc.) for a determined or specified period of time (e.g., 7 days, 1 month, 180 days, or other time period). Optionally, the health timeline may be configured so that it is linear (where a unit of distance is equal to a set amount of time) or is non-linear in terms of time. For example, the timeline may be a logarithmic where the timeline is laid out according to a logarithmic scale such that the time axis itself is plotted logarithmically so that more recent time periods (and associated diagnosis and/or treatment data) may be provided with relatively more space on the timeline than older time periods.

Optionally, the health timeline may be zoomable to focus on a particular time period and to display additional entries for a given time period. For example, the timeline may be zoomable via a user interface that enables the user to use a lasso or other tool to indicate a beginning and end portion of the timeline that is to be zoomed. Optionally, in addition or instead, the user interface enables the user to numerically specify a numerical zoom factor and/or to use a touch interface to stretch/zoom out a given portion of the health timeline by touching one end of the portion with a thumb, touching the other end of the portion with a finger, and then moving the thumb and finger apart. Optionally, a selected portion of the health timeline may be generated and displayed at a higher time resolution at the same time the original timeline is displayed at the original resolution, as illustrated in FIG. 4C. Optionally, a given timeline entry may be selectable (e.g., clickable), wherein in response to a user selection, additional information regarding the selected entry is accessed and displayed (e.g., for a medical test, the test results and/or scans may be accessed and displayed).

FIGS. 4S2 and 4S3 illustrates an example master combined introduction user interface and timeline user interface. The master/combined user interface merges some or all of the information from the Biographical, Medical, Clinical, Therapeutic, Diary, and/or other sections of the notebook into a unified timeline that lists the events, treatments, and other information with associated dates and/or times. Thus, the master combined user interface provides an overall snapshot for the patient. Optionally, the master combined user interface may be similar in appearance to the health timeline, with additional information. The master combined user interface may include all or a subset of the information included in the health timeline.

The generated master combined user interface may include a timeline that begins at a certain point in time, such as a significant biological date (e.g. date of birth of the patient), and may indicate, in chronological order, significant biographical information (e.g., where and when the patient went to school, when the patent was married, how many children the patient has and when each child was born, when and where the patient has been employed, whether the patient's parents are still alive, and if not when a given parent died, etc.), diagnosis dates, medical intervention/treatment dates, diary entries, listings of appointments with medical professionals (e.g., therapist, psychiatrist or psychologist, and their name), treatment frequency, psychological and/or other patient testing, etc. Optionally, the master combined user interface may be updated in real time in response to the receipt of new or updated biographical, medical, clinical, therapeutic, and/or diary data. Optionally, new or updated information may be emphasized (e.g., by color, font, icon, etc.) for a determined or specified period of time after being received or initially displayed (e.g., 7 days, 1 month, 180 days, or other time period). Optionally, the master combined user interface timeline may be configured so that it is linear (where a unit of distance is equal to a set amount of time) or is non-linear in terms of time. For example, the timeline may be a logarithmic where the timeline is laid out according to a logarithmic scale such that the time axis itself is plotted logarithmically so that more recent time periods (and associated diagnosis and/or treatment data) may be provided with relatively more space on the timeline than older time periods.

Optionally, the master combined user interface timeline (and/or the health timeline) may be zoomable to focus on a particular time period and to display additional entries for a given time period. Optionally, the user interface enables the user to numerically specify a numerical zoom factor and/or to use a touch interface to stretch/zoom out a given portion of the timeline by touching one end of the portion with a thumb or other digit, touching the other end of the portion with a finger or other digit, and then moving the thumb and finger apart. Similarly, the user interface may enable the user to zoom in on a given portion using a pinch gesture, by touching one end of the portion with a first digit (e.g., a thumb), touching the other end of the portion with a second digit (e.g., a finger), and then moving the two digits (e.g., thumb and finger) together. As similarly discussed above with respect to the health timeline, optionally, the timeline may be zoomable via a user interface that enables the user to use a lasso or other tool to indicate a beginning and end portion of the timeline that is to be zoomed. Optionally, a selected portion of the timeline may be generated and displayed at a higher time resolution at the same time the original timeline is displayed at the original resolution, as illustrated in FIG. 4S. Optionally, a given timeline entry may be selectable (e.g., clickable), wherein in response to a user selection, additional information regarding the selected entry is accessed and displayed (e.g., for an appointment, a calendar entry may open showing the time, date, location and/or other information).

FIG. 4T illustrates an example check-in user interface. The check-in user interface facilitates communication between a user/patient and a treating professional. For example, the check-in user interface may enable the user to provide updates on how the patient is doing. The treatment professional may also designate, via an authorization user interface, support staff to receive the check-in information on patient-by-patient basis, for all patients, or for specific classes of patients (e.g., information for adult patients, but not minors). In the event that support staff is designated or authorized to assist the treatment professional in the patient communication, the appropriate members of the support staff may also added to the notebook contact data store in association with an indication as to which treatment professional they are associated with.

The check-in user interface may include the following selectable options with respect to who is performing the check-in: Patient; or Significant Other/Care Giver/Family Member. The selected option may be communicated to the check-in information recipient so that the recipient will know who is providing the check-in information. The check-in frequency may be scheduled and the schedule may be determined based at least in part on a recommendation of the treating professional. The schedule may be entered into the notebook calendar (e.g., via the treatment plan section of the notebook). The notebook will then provide an alert or cue (e.g., via a pop-up alert, an SMS/MMS message, an email message, etc.) to one or more designated alert recipients (e.g., the patient, the patient's significant other, child, caretaker, etc.) that it is time to check-in. The alert may be provided on the scheduled check-in day and/or a certain period of time (e.g., a certain number of days) prior to the check-in day. Check-in may also be performed in an unscheduled manner (e.g., based on perceived need by the patient).

A field may be provided configured to receive free-form text via which the check-in information may be provided. Natural language or keyword processing may be utilized to identify (e.g., with a certain likelihood percentage) that words or phrases used in the information provided during the check-in (e.g., by the patient, significant other, caregiver, family member), or slurred or unintelligible speech, indicate an elevated or immediate need for attention. If the processing detects such an elevated or immediate need for attention, an alert may be provided to the treating professional (e.g., via a pop-up alert, an SMS/MMS message, an email message, etc.), where the alert may indicate that the check-in information needs to be urgently reviewed, and that the patient may need immediate attention. For example, words and phrases that indicate urgency may include some or all of the following terms and/or other terms: hopeless, worthless, suicidal, anxious, depressed, afraid, helpless, afraid, out-of-control, gun, knife, rage, violent, etc. By way of further example, urgency may be indicated if system or app detects that the information provided via the check-in user interface is unintelligible or the speech (e.g., slurred speech) or text patterns indicate that the user is engaging in substance abuse (e.g., of drugs or alcohol) or is suffering a stroke. The alert may be dynamically generated and composed to include the keywords/terms that triggered the alert, and/or may indicate that unintelligible/slurred speech was detected. Speaker-adaptive, continuous speech recognition may be utilized in converting speech to text.

Optionally, if the app or system detects that the patient has not checked at the specified interval or schedule, an alert may be generated and provided to the treating professional and/or team leader indicating that the patient failed to check-in as specified. An alert may also be provided to the patient and other designated recipient with a request to check-in.

With reference to the example user interface illustrated in FIG. 4U, if the patient check-in option was selected, the check-in user interface may be configured to include fields that prompt the patient (or the patient's caretaker) to indicate if the patient knows how the patient feels, to describe how the patient feels, to indicate what treatment the user feels is working in a beneficial manner, to indicate what treatment the user feels (e.g., subjectively feels) is not working in a beneficial manner or is having an adverse effect, to indicate what the patient feels (e.g., subjectively feels) is going or working well in the patient's life, to indicate what is not going or working well in the patient's life, what others do not know about what is going on with the patient, how the patient feels physically, etc. Collecting and analyzing patterns with respect to the patient's subjective sense on how the patient is doing, what is working for the patient, and what is not working for the patient can be very helpful in understanding and treating the patient (e.g., sometimes as helpful or more helpful than the patient's clinical symptoms). Optionally, an analysis may be performed to identify a frequency/clustering of a patient's subjective feelings of wellbeing or feelings of illness or lack of wellbeing. The clustering (e.g., peaks of a certain subjective feeling over a period of time) may then be utilized to identify current or predict future time periods that may be difficult for or result in a sense of a lack of wellbeing on the part of the patient.

If the Significant Other/Caregiver/Family Member option was selected, the check-in user interface may be configured to include fields that prompt the non-patient user to indicate how the patient is generally doing, what are the user's most significant concerns regarding the patient, how the user is feeling, what the user thinks the patient is not telling the treating professional, what the user needs help with, etc.

The check-in section of the notebook may be configured to enable real-time or recorded videos or images (optionally with an associated voice track) of the patient and/or significant other/caregiver/family member to be transmitted to the treatment provider and/or support staff terminals to enable them to visually see and assess the patient and/or significant other/caregiver/family member. Such visual content may provide significant or critical information in making mental and/or physical health assessments (e.g., enable the treatment provider to detect if someone has suffered a stroke or heart attack, or is suffering from drug abuse). Optionally, some or all of the information provided via the fields described above may in addition or instead be provided via the visual content, optionally including a corresponding sound track (of the patient or non-patient speaking). The visual content may optionally be time-stamped indicating what day and time it was recorded and/or transmitted. A record control may be provided to initiate a video or image recording via the camera on the user terminal.

Figure 4V:

FIG. 4V illustrates an example new information user interface. A user interface may be provided enable a user to receive information about the user's area of concern. The user may explicitly submit a description of the area of concern, select an area of concern from a menu provided via the notebook, or the notebook or remote system may infer the area of concern from information received via one or more of the other notebook sections (e.g., based on the medical condition selected, the list section, the referral section, the contacts section, the wall section, the treatment plan section, the medication section, the treatment section, etc.). The system will search for and access new information corresponding to the area of concern, and cause the new information to be presented via the new information user interface. An item of information may be categorized by the system as new if it has been posted or otherwise made available no more than a specified threshold period of time (e.g., the last 60 days) or since the user last accessed the new information user interface. The new information may include a wide variety of views and/or scientific opinion from a wide variety of sources (e.g., institutions and people). Optionally, a validation/credibility determination process may be performed for a given item of new information prior to presenting the information via the new information user interface.

FIG. 4W illustrates an example biographical user interface via which a patient can provide the patient's overall life story. The biographical user interface may include fields via which the patient can specify some or all of the following: ethnicity, where the patient's parents were born (e.g., country, state, city, etc.), if there were or are any special problems in the patient's family of origin, if there were or are any health problems or illness in the patient's family of origin, where the patient was born (e.g., country, state, city, etc.), whether the patient has any siblings and if so there gender, ages, if they are currently alive, cause of death and/or other details, if there were there any deaths in your family that were unexplained, the places the patient has lived since your birth (e.g., country, state, city, etc.), and/or other biographical information.

FIG. 4X illustrates an example financial ("money matters") user interface which may be used to indicate the source of payments (e.g., private insurance, government funding, self-funding, etc.). The financial section enables the patient (or non-patient) to record insurance information that will aid the person in submitting claims to an insurance company and in keeping track of what claims the insurance company has paid to-date and what claims need follow-up or additional information.

The financial user interface may include fields via which some or all of the following may be specified: an indication as to whether the patient has insurance, and if so the corresponding insurance information (e.g., the identification number, Rx Bin, Rx PCN, Rx Group, Plan code, Group number, etc.). The financial user interface may also prompt the user (the patient or non-patient user) to indicate whether the user wants to the use the notebook for keeping track of insurance billing matters. If the user responds affirmatively, the user may be prompted to provide claim information (e.g., receipts, itemized bills, what the treatment or visit was for, to whom is payment to be made, etc.).

The financial user interface may also prompt the user to indicate whether the patient has disability coverage or Long Term Disability Coverage (LTD), and if so, provide related information (e.g., the insurance provider, the policy number, etc.). If the user does have LTD coverage, the financial user interface may also prompt the user to indicate whether the user wants to utilize the notebook to keep track of the patient's related claims. If the user indicates that the user wants to utilize the notebook to keep track of the patient's LTD claims, the user is requested to provide information regarding the claims (e.g., evidence that the patient is disabled and the nature of the disability, such as a doctor's statement or form regarding the doctor's opinion on the patient's condition, evidence that the patient had been employed when the disability occurred, evidence that any waiting period has expired, etc.).

The financial user interface may also prompt the user to indicate whether the patient has Supplemental Security Income (SSI), and if so, to provide related information, such as the patient's income, the patient's assets, the patient's living arrangements, the patient's citizenship or alien status, the patient's health issues and how they affect the patient's daily activities and ability to work, etc. If the user does have SSI, the financial user interface may also prompt the user to indicate whether the user wants to utilize the notebook to keep track of the patient's related SSI claims. If the user indicates that the user wants to utilize the notebook to keep track of the patient's SSI claims, the user is requested to provide information regarding the claims.

The financial user interface may also prompt the user to indicate whether the patient has Social Security Disability Insurance (SSDI), and if so, to provide related information, such as the patient's Social Security number and proof of the patient's age, names, addresses and phone numbers of doctors, caseworkers, hospitals, and clinics that took care of the patient and the dates of appointments, names and dosages of the medications the patient is taking, medical records laboratory and test results, a summary of where the patient worked and the kind of work the patient did, the patient's most recent W-2 form or, if self-employed, a copy of the patient's federal tax return, information about the patient's family members, Social Security numbers and proof of age for each family member who may qualify for benefits, etc. If the user does have SSDI, the financial user interface may also prompt the user to indicate whether the user wants to utilize the notebook to keep track of the patient's related SSDI claims. If the user indicates that the user wants to utilize the notebook to keep track of the patient's SSDI claims, the user is requested to provide information regarding the claims.

A grid may be generated and displayed configured to aid in the tracking of claims and payments made to treatment providers, including the payment amounts and payment dates. For example, the grid rows may correspond to respective treatment providers, and the columns may correspond to payment dates (or vice versa). A given grid cell may list a payment amount (e.g., a payment made or due). Thus, the grid may provide an "at a glance" summary of payments made and payments due enabling a patient/caretaker or other user that has financial responsibility with respect to the patient.

FIG. 4Y illustrates an example resources user interface configured to provide a directory of resources (which may be in the form of linked text that can be activated to access more detailed information). The display of the resources may be organized by, diagnosis or cluster of diagnosis, type of specialty or need, etc. The resource user interface may also include a search field enabling the user also be used to search for and/or display resources from the resource directory depending upon the patient's geographical needs (e.g., within a specified region, city, zip code, a specific number of miles from the patient's residence and/or from the device hosting the notebook, etc.).

FIG. 4Z illustrates an example team user interface configured to enable a support team to be defined for a patient. For example, the team user interface may include fields via which names may be added (e.g., via a contact database) for members of the team and where tasks may be associated with a given team member. Example tasks may include providing transportation for the patient to medical appointments, providing meals for the patient, following-up with the patient to ensure the patient is taking the prescribed medication and performing the prescribed therapy, etc. A given team member may be designated as a team leader. The team leader may be automatically informed of patient-related events entered into the notebook, such as medical tests (e.g., scans, blood tests, biopsies, etc.) and test results, admissions to hospitals, medical referrals, newly prescribed medications, termination of medications, newly prescribed therapies (e.g., physical therapy, speech therapy, counseling sessions, etc.), termination of therapies, changes in the patient's living situation (e.g., the patient has moved, some new is living with the patient, etc.), etc. This enables the team leader to be more informed regarding the patient's changing situation, to comment on such changes, and to communicate with the patient, the patient's medical professionals, the patient's family, the patient's caretaker, other team members, etc., regarding the changes and potential actions that should be taken.

Figure 3B:
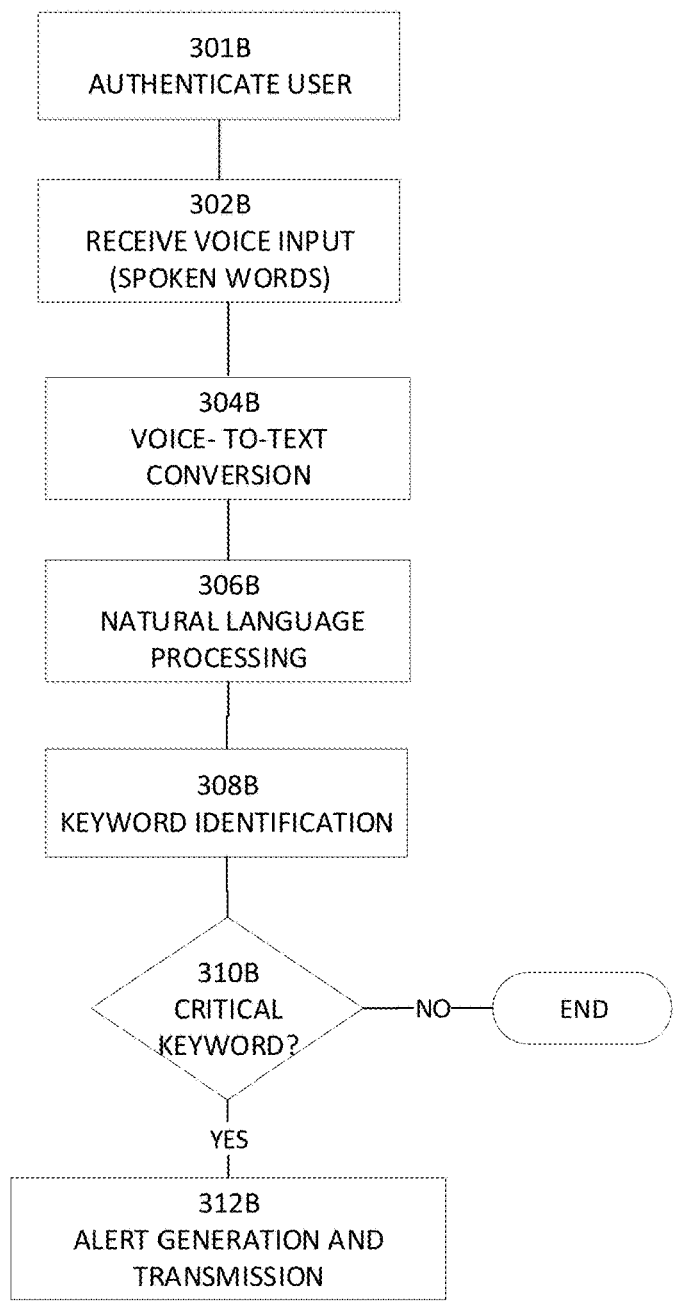
FIG. 3B illustrates an example process.

FIG. 3B illustrates an example process for identifying alert conditions using natural language processing and keyword identification based on user input. At block 301B, the user is authenticated as similarly described above using facial recognition on a captured image of the user or by scanning and comparing the user's fingerprint. The user input may be provided via voice, touch (e.g., via a human digit or stylus), keyboard, a combination of two or more of the foregoing, or otherwise. If user input is being received as a voice input (spoken words) via microphone, than at block 302B, the voice input is received and at block 304B, speech-to-text conversion is performed (e.g., by the user terminal and/or by a remote system). As discussed elsewhere herein, the speech-to-text conversion process may be performed using one or more of pattern matching, pattern and feature analysis, language modeling and statistical analysis, and/or neural networks. Optionally, speaker-adaptive, continuous speech recognition may be utilized in converting speech to text.

At block 306B, natural language processing is optionally performed on the user input (e.g., touch input, keyboard input, or the text generated by the speech-to-text process). At block 308B, keyword identification is performed (e.g., keywords that indicate the topic of the user input or that indicate an emotion or feeling of wellbeing). At block 310B a determination is made as to whether the identified keywords in the user input indicate a critical/safety related condition. The keyword criticality determination may be performed by comparing the user input against a data store of keywords that indicate a potential critical condition. For example, the keyword data store may include some or all of the following keywords (or key phrases): hopeless, worthless, suicidal, anxious, depressed, afraid, helpless, afraid, out-of-control, gun, knife, rage, furious, violent, drinking, drunk, drugged, scream, out-to-get-me, etc. A given keyword may be associated with a condition type, such as a psychological condition, a pharmaceutical condition, an orthopedic condition, etc. Optionally, a critically determination may weight different keywords differently, and the criticality determination may optionally calculate a criticality score based on the number of keywords and the keyword weighting. If the criticality score exceeds a specified threshold, a determination may be made that a potential critical condition. For example, the following formula may be used:

Criticality Score=Weght$^1$(of Keyword$^1$)+Weght$^2$(of Keyword$^2$) . . . +Weght$^n$(of Keyword$^n$)

Where a potential critical condition exists if Criticality Score≥Criticality Score If the keyword criticality determination identifies a potential critical condition, at block 312B, an alert may be dynamically generated and transmitted to one or more destinations based on one or more rules accessed from a rule data store. For example, a rule may indicate that all alerts are to be transmitted to a previously identified caretaker/family member and a previously identified primary physician. Another rule may indicate that if a keyword is associated with a physiological condition, then an alert is to be transmitted to a specified psychiatrist or psychologist.

Thus, processes and techniques are described that may be used to receive, manage and process the recording, arrangement, text processing, word recognition, and/or review of information for or in an electronic notebook.

The methods and processes described herein may have fewer or additional steps or states and the steps or states may be performed in a different order. Not all steps or states need to be reached. The methods and processes described herein may be embodied in, and fully or partially automated via, software code modules executed by one or more general purpose computers. The code modules may be stored in any type of computer-readable medium or other computer storage device. Some or all of the methods may alternatively be embodied in whole or in part in specialized computer hardware. The systems described herein may optionally include displays, user input devices (e.g., touchscreen, keyboard, mouse, voice recognition, etc.), network interfaces, etc.

The results of the disclosed methods may be stored in any type of computer data repository, such as relational databases and flat file systems that use volatile and/or non-volatile memory (e.g., magnetic disk storage, optical storage, EEPROM and/or solid state RAM).

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "may," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

While the phrase "click" may be used with respect to a user selecting a control, menu selection, or the like, other user inputs may be used, such as voice commands, text entry, gestures, etc. User inputs may, by way of example, be provided via an interface, such as via text fields, wherein a user enters text, and/or via a menu selection (e.g., a drop down menu, a list or other arrangement via which the user can check via a check box or otherwise make a selection or selections, a group of individually selectable icons, etc.). When the user provides an input or activates a control, a corresponding computing system may perform the corresponding operation. Some or all of the data, inputs and instructions provided by a user may optionally be stored in a system data store (e.g., a database), from which the system may access and retrieve such data, inputs, and instructions. The notifications/alerts and user interfaces described herein may be provided via a Web page, a dedicated or non-dedicated phone application, computer application, a short messaging service message (e.g., SMS, MMS, etc.), instant messaging, email, push notification, audibly, a pop-up interface, and/or otherwise.

The user terminals described herein may be in the form of a mobile communication device (e.g., a cell phone), laptop, tablet computer, interactive television, game console, media streaming device, head-wearable display, networked watch, etc. The user terminals may optionally include displays, user input devices (e.g., touchscreen, keyboard, mouse, voice recognition, etc.), network interfaces, etc.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A communication system, the communication system comprising:
   a processor device;
   non-transitory computer readable medium that stores instructions configured to cause the processor device to perform operations comprising:
   establishing an encrypted transmission over a wireless network between the communication system and a cloud system using a secure transfer mechanism;
   authenticating a user using an authentication system, the authentication system configured to:
   capture an image of the user using a camera, extract features of the user from the image, determine whether the extracted features correspond to features of an authorized user, and if so, identify the user as the authorized user; or
   scan of a fingerprint of the user using a fingerprint scanner,
   determine whether the fingerprint of the user using the communication system corresponds to an authorized user, and if so, identify the user as the authorized user;
   wirelessly accessing, using the secure transfer mechanism, user medical data from a plurality of sources stored on the cloud system at least partly in response to authenticating that the user is the authorized user;
   generating a user interface rendering at least a portion of the user medical data from the plurality of sources using a zoomable patient health timeline configured to be zoomed in response to a gesture made using two fingers, the zoomable patient health timeline comprising:
   medical appointment entries,
   medical diagnosis entries, and
   treatment entries;
   detecting a user selection of a first medical appointment on the generated zoomable patient health timeline;
   in response to detecting the user selection of the first medical appointment on the generated zoomable patient health timeline, opening and displaying a corresponding calendar entry, including time, date, and location information;
   in response to receiving a user zoom instruction on to the zoomable patient health timeline to select a first portion of the timeline, the user zoom instruction comprising a first gesture, causing the first portion of the zoomable patient health timeline to be displayed at a first resolution in a first region together with a display of the original zoomable patient health timeline at a second resolution displayed in a second region separate from the first region;
   receiving new medical data;
   utilizing the secure transfer mechanism to wirelessly synchronize the received new medical data with user medical data stored on the cloud system at partly in response to detecting a first event;
   enabling the zoomable patient health timeline to be updated with the new medical data, wherein the new medical data is visually emphasized relative to other health timeline data for a first period of time;
   storing a first calendar entry, including a second medical appointment timing, associated with a second medical appointment;
   receiving one or more questions from the user as a voice input for the second medical appointment;
   using a voice-to-text application hosted by the cloud system to convert the voice input from the user to text, the text comprising questions;
   receiving, over the wireless network from the cloud system, the text comprising questions, corresponding to the voice input from the user;
   populating one or more user interface fields in a first user interface using the text received from the cloud system;
   providing an interface enabling the user to share the text received from the cloud system with a first recipient;
   detecting an occurrence of the second medical appointment timing associated with the second medical appointment; and
   at least partly in response to detecting the occurrence of the second medical appointment timing associated with the second medical appointment, displaying at least a portion of the text comprising questions received from the cloud system via a display.

2. The communication system as defined in claim 1, the operations further comprising:
   generating a data sharing user interface configured to share information from a plurality of sources regarding medical matters with other users;

the data sharing user interface comprising:
- a search field configured to receive a user search query enabling the user to search through postings regarding the medical matters;
- a search filter user interface comprising predefined search filters, the search filters including one or more medical diagnosis or medical conditions;
- a posting field configured to receive information to be posted;
- a tag field configured to receive a tag to be associated with the received information to be posted;
- a favorite control that enables the user to designate a posting or a posting user as a favorite;

conducting, using the cloud system, a search using the user search query and one or more user-selected search filters; and providing search results filtered in accordance with the user-selected one or more search filters for display.

3. The communication system as defined in claim 1, the operations further comprising:
encrypting user data;
storing the encrypted user data in a first computer system; and
enabling a key associated with the encrypted user data to be stored on a computer system physically separate from the first computer system.

4. The communication system as defined in claim 1, the operations further comprising:
converting, using the cloud system, the voice input from voice to text using natural language processing,
the natural language processing comprising determining a probability of certain words or sounds following on from one another to thereby speed up word recognition and improve recognition accuracy.

5. The communication system as defined in claim 1, the operations further comprising:
converting, using the cloud system, the voice input from voice to text via a natural language processing system comprising a neural networking trained to recognize patterns comprising word sounds to improve the natural language processing system's ability to understand the voice input.

6. The communication system as defined in claim 1, the operations further comprising:
providing a team user interface that enables:
- a medical team comprising a plurality of team members to be defined for the user;
- respective tasks to be associated with respective members of the medical team;
- a designation of a team leader;

receiving, via the team user interface, a medical team definition and a team leader designation;
using a second voice input from the user in detecting a first user condition;
enabling an alert, including text corresponding to at least a portion of the voice input from the user, to be transmitted to at least the designated team leader; and
enabling members of the defined medical team to communicate with each other and access data related to the user.

7. The communication system as defined in claim 1, the operations further comprising:
accessing user data comprising:
diagnosis dates,
medical intervention dates,
generating the zoomable patient health timeline comprising a plurality of items using the accessed user data;
detecting a user selection of an item from the plurality of items on the generated zoomable patient health timeline; and
causing additional information regarding the zoomable patient health timeline item selection to be presented.

8. The communication system as defined in claim 1, the operations further comprising:
generating a calendar entry for a third medical appointment;
recording audio content related to the third medical appointment using a microphone of the communication system;
transmitting the audio content to the cloud system using the secure transfer mechanism;
using the cloud system to perform natural language processing comprising language modeling and statistical analysis to convert the audio content to text; and
adding the text, one or more medical test results, and one or more prescriptions to the calendar entry for the third medical appointment.

9. The communication system as defined in claim 1, the operations further comprising:
recording audio content of a medical professional at a third medical appointment;
transmitting the audio content to the cloud system using the secure transfer mechanism;
using the cloud system to perform natural language processing comprising language modeling and statistical analysis to convert the audio content of the medical professional to text;
determining, using the cloud system, if the text includes a recommendation; and
at least partly in response to a determination that the text includes the recommendation, adding the recommendation to an electronic to-do list.

10. The communication system as defined in claim 1, the operations further comprising:
generating a calendar entry for a third medical appointment;
recording video and audio content related to the third medical appointment using the communication system camera and microphone; and
associating a timestamp with the recorded video and audio content; and
adding the video and audio content to the calendar entry for the third medical appointment.

11. The communication system as defined in claim 1, the operations further comprising:
receiving referral contact information for a first medical provider;
automatically augmenting at least one calendar entry with at least a portion of the referral contact information.

12. A computer implemented method, the method comprising:
establishing, using a network interface of a mobile computer system, an encrypted transmission over a wireless network between the mobile computer system and a cloud system using a secure transfer mechanism;
authenticating a user by using an authentication system of the mobile computer system configured to:
capture an image of the user using a mobile computer system camera,
extract features of the user from the image,
determine whether the extracted features correspond to features of
an authorized user, and if so, identify the user as the authorized user; or scan of a fingerprint of the user using a fingerprint scanner,
determine whether the fingerprint of the user using the mobile computer system corresponds to an authorized user, and if so, identify the user as the authorized user;
enabling the mobile computer system to wirelessly access, using the secure transfer mechanism, user medical data from a plurality of sources stored on the cloud system at least partly in response to authenticating that the user is the authorized user;
generating a user interface rendering at least a portion of the user medical data from the plurality of sources using a zoomable timeline configured to provide a quick overview of the user's medical history, the zoomable timeline comprising:
medical appointment entries,
medical diagnosis entries, and
treatment entries;
detecting a user selection of a first medical appointment on the generated zoomable timeline;
in response to detecting the user selection of the first medical appointment on the generated zoomable timeline, opening and displaying a corresponding calendar entry, including time, date, and location information;
in response to receiving a user zoom instruction on the generated zoomable timeline to select a first portion of the generated zoomable timeline, the user zoom instruction comprising a first gesture, causing the first portion of the generated zoomable timeline to be displayed at a first resolution in a first region together with a display of the original generated zoomable timeline at a second resolution displayed in a second region separate from the first region;
receiving new medical data via the mobile computer system;
utilizing the secure transfer mechanism to wirelessly synchronize the received new medical data on the mobile computer system with data stored on the cloud system at partly in response to detecting a first event;
enabling the zoomable timeline to be updated with the new medical data, wherein the new medical data is visually emphasized relative to other zoomable timeline data for a first period of time;
storing a first calendar entry associated with a second medical appointment associated with a second medical appointment timing;
receiving a voice input from the user for the second medical appointment;
using a voice-to-text application hosted by the cloud system to convert the voice input from the user to text;
receiving, over the wireless network from the cloud system, text corresponding to the voice input from the user;
populating one or more user interface fields in a first user interface using the text received from the cloud system;
providing an interface enabling the user to share the text received from the cloud system with a first recipient;
detecting an occurrence of the second medical appointment timing associated with the second medical appointment; and
at least partly in response to detecting the occurrence of the second medical appointment timing associated with the second medical appointment, enabling at least a portion of the text to be displayed.

13. The method as defined in claim 12, the method further comprising:
at least partly in response to detecting the occurrence of the second medical appointment timing associated with the second medical appointment, displaying at least a portion of the text, comprising user questions, received from the cloud system via a display of the mobile computer system.

14. The method as defined in claim 12, the method further comprising:
receiving at the cloud system a task;
identifying a source of data associated with the task; and
assigning the task to a cloud node based at least in part on a geo proximity of the cloud node to the source of data associated with the task.

15. The method as defined in claim 12, the method further comprising:
encrypting user data;
storing the encrypted user data in a first computer system; and
storing a key associated with the encrypted user data on a computer system physically separate from the first computer system.

16. The method as defined in claim 12, the method further comprising: converting, using the cloud system, the voice input from voice to text using natural language processing, the natural language processing comprising determining a probability of certain words or sounds following one from one another to thereby speed up word recognition and improve recognition accuracy.

17. The method as defined in claim 12, the method further comprising: converting, using the cloud system, the voice input from voice to text via a natural language processing system comprising a neural networking trained to recognize patterns comprising word sounds to improve the natural language processing system's ability to understand the voice input.

18. The method as defined in claim 12, the method further comprising:
providing a team user interface that enables:
a medical team comprising a plurality of team members to be defined for the user;
respective tasks to be associated with respective members of the medical team;
a designation of a team leader;
receiving, via the team user interface, a medical team definition and a team leader designation;
detecting, using a second voice input from the user, a first user condition;
transmitting an alert, including text corresponding to at least a portion of the voice input from the user to at least the designated team leader; and
enabling members of the defined medical team to communicate with each other and access data related to the user.

19. The method as defined in claim 12, the method further comprising:
accessing user data comprising:
diagnosis dates, and
medical intervention dates,
generating the zoomable timeline comprising a plurality of items using the accessed user data;
detecting a user selection of an item on the generated zoomable timeline; and
causing additional information regarding the timeline item selection to be presented.

20. The method as defined in claim 12, the method further comprising:

generating a calendar entry for a third medical appointment;
recording audio content related to the third medical appointment using a microphone of the mobile computer system;
transmitting the audio content from the mobile computer system using the network interface to the cloud system using the secure transfer mechanism;
using a trainable computer model hosted on the cloud system to perform natural language processing comprising language modeling and statistical analysis to convert the audio content to text; and
adding the text, one or more medical test results, and one or more prescriptions to the calendar entry for the third medical appointment.

21. The method as defined in claim 12, the method further comprising:
recording audio content of a medical professional at a third medical appointment using a microphone of the mobile computer system;
transmitting the audio content from the mobile computer system using the network interface to the cloud system using the secure transfer mechanism;
using the cloud system to perform natural language processing comprising language modeling and statistical analysis to convert the audio content of the medical professional to text;
determining, using the cloud system, if the text includes a recommendation; and
at least partly in response to a determination that the text includes the recommendation, adding the recommendation to an electronic to-do list.

22. The method as defined in claim 12, the method further comprising:
generating a calendar entry for a third medical appointment;
recording video and audio content related to the third medical appointment using the mobile computer system camera and microphone; and
associating a timestamp with the recorded video and audio content; and
adding the video and audio content to the calendar entry for the third medical appointment.

23. The method as defined in claim 12, the method further comprising:
receiving referral contact information for a first medical provider;
automatically augmenting at least one calendar entry with at least a portion of the referral contact information.

24. A computer implemented method, the method comprising:
initiating, using a network interface of a computer system, an encrypted transmission over a wireless network between the computer system and a cloud system using a secure transfer mechanism;
authenticating a user;
enabling the computer system to wirelessly access, using the secure transfer mechanism, user medical data from a plurality of sources stored on the cloud system at least partly in response to authenticating that the user is the authorized user;
generating a user interface rendering at least a portion of the user medical data from the plurality of sources using a zoomable timeline having a first resolution, the zoomable timeline configured to provide an overview of the user's medical history, the zoomable timeline comprising:
medical appointment entries,
detecting a user selection of a first medical appointment on the generated zoomable timeline;
in response to detecting the user selection of the first medical appointment on the generated zoomable timeline, opening and displaying a corresponding calendar entry, including time, date, and location information;
receiving new medical data via the computer system;
utilizing the secure transfer mechanism to wirelessly synchronize the received new medical data on the computer system with data stored on the cloud system at partly in response to detecting a first event;
enabling the zoomable timeline to be updated with the new medical data, wherein the new medical data is visually emphasized relative to other timeline data for a first period of time;
storing a first calendar entry, including a second medical appointment timing, associated with a second medical appointment;
receiving a voice input from the user for the second medical appointment;
using a voice-to-text application hosted by the cloud system to convert the voice input from the user to text;
receiving, over the wireless network from the cloud system, text corresponding to the voice input from the user;
populating one or more user interface fields in a first user interface using the text received from the cloud system;
providing an interface enabling the user to share the text received from the cloud system with a first recipient;
detecting an occurrence of the second medical appointment timing associated with the second medical appointment; and
at least partly in response to detecting the occurrence of the second medical appointment timing associated with the second medical appointment, enabling at least a portion of the text to be displayed;
causing the user to be prompted, using a first prompt, to provide medical status information;
receiving, via a microphone on the computer system, a first spoken response to the first prompt from the user, the first spoken response comprising a first sequence of words;
transmitting the first spoken response to the first prompt from the computer system over the network to the cloud system using the secure transfer mechanism;
performing, using the cloud system, natural language processing, comprising language modeling and statistical analysis, on the received first spoken response comprising the first sequence of words to convert the first spoken response to text;
identifying, using the cloud system, one or more keywords in the first sequence of words to at least determine if the first sequence of words includes patient concerns;
generating, using the cloud system, a criticality score using the keywords identified in the first sequence of words and respective criticality keyword weightings, wherein a first keyword in the first sequence of words is associated with a first criticality weight and a second keyword in the first sequence of words is associated with a second criticality weight;
identifying, using the cloud system, an urgent user condition based at least in part on the criticality score generated using the keywords identified in the first sequence of words and the respective keyword criticality weightings;

dynamically generating, using the cloud system, an alert based at least in part on the identified user urgent condition, wherein the dynamically generated alert comprises one or more of the keywords identified in the first sequence of words; and transmitting, using the cloud system, the dynamically generated alert, including the one or more of the keywords identified in the first sequence of words, using the network interface to one or more destinations.

25. Non-transitory memory that stores instructions that when executed by a computer system are configured to cause the computer system to perform operation comprising:

establishing an encrypted transmission over a wireless network between the computer system and a remote system using a secure transfer mechanism;

authenticating a user using an authentication system, the authentication system configured to:
  capture an image of the user using a camera,
  extract features of the user from the image,
  determine whether the extracted features correspond to features of an authorized user, and if so, identify the user as the authorized user; or
  scan of a fingerprint of the user using a fingerprint scanner,
  determine whether the fingerprint of the user using the computer system corresponds to an authorized user, and if so, identify the user as the authorized user;

wirelessly accessing, using the secure transfer mechanism, user medical data from a plurality of sources stored on the remote system at least partly in response to authenticating that the user is the authorized user;

generating a user interface rendering at least a portion of the user medical data from the plurality of sources using a zoomable timeline configured to be zoomed in response to a gesture made using two fingers, the zoomable timeline comprising:
  medical appointment entries,
  medical diagnosis entries, and
  treatment entries;

detecting a user selection of a first medical appointment on the generated zoomable timeline;

in response to detecting the user selection of the first medical appointment on the generated zoomable timeline, opening and displaying a corresponding calendar entry, including time, date, and location information;

in response to receiving a zoom instruction on the generated zoomable timeline to select a first portion of the generated zoomable timeline, the user zoom instruction comprising a first gesture, causing the first portion of the zoomable timeline to be displayed in a first region at a first resolution together with a display of the original zoomable timeline at a second resolution displayed in a second region separate from the first region;

receiving new medical data;

utilizing the secure transfer mechanism to wirelessly synchronize the received new medical data with data stored on the remote system at partly in response to detecting a first event;

enabling the zoomable timeline to be updated with the new medical data, wherein the new medical data is visually emphasized relative to other timeline data for a first period of time;

storing a first calendar entry, including a second medical appointment timing, associated with a second medical appointment;

receiving a voice input from the user for the second medical appointment;

using a voice-to-text application hosted by the remote system to convert the voice input from the user to text;

receiving, over the wireless network from the remote system, text corresponding to the voice input from the user;

populating one or more user interface fields in a first user interface using the text received from the remote system;

detecting an occurrence of the second medical appointment timing associated with the second medical appointment; and at least partly in response to detecting the occurrence of the second medical appointment timing associated with the second medical appointment, displaying at least a portion of the text received from the remote system via a display.

26. The non-transitory memory as defined in claim 25, the operations further comprising:

generating a data sharing user interface configured to share information from a plurality of sources regarding medical matters with other users;

the sharing user interface comprising:
  a search field configured to receive a user search query enabling a user to search through postings regarding the medical matters;
  a search filter user interface comprising predefined search filters, the search filters including one or more medical diagnosis or medical conditions;
  a posting field configured to receive information to be posted;
  a tag field configured to receive a tag to be associated with the received information to be posted;
  a favorite control that enables the user to designate a posting or a posting user as a favorite;

initiating a search using the user search query and one or more user-selected search filters; and providing search results filtered in accordance with the user-selected one or more search filters for display.

27. The non-transitory memory as defined in claim 25, the operations further comprising:

converting, using the remote system, the voice input from voice to text using natural language processing, the natural language processing comprising determining a probability of certain words or sounds following on from one another to thereby speed up word recognition and improve recognition accuracy.

28. The non-transitory memory as defined in claim 25, the operations further comprising:

accessing user data comprising:
  diagnosis dates, and
  medical intervention dates, generating the zoomable timeline comprising a plurality of items using the accessed user data;

detecting a user selection of an item on the generated zoomable timeline; and causing additional information regarding the timeline item selection to be presented.

29. The non-transitory memory as defined in claim 25, the operations further comprising:

recording audio content of a medical professional at a third medical appointment;

transmitting the audio content to the remote system using the secure transfer mechanism;

using the remote system to perform natural language processing comprising language modeling and statistical analysis to convert the audio content of the medical professional to text;

determining, using the remote system, if the text includes a recommendation; and at least partly in response to a determination that the text includes the recommendation, adding the recommendation to an electronic to-do list.

\* \* \* \* \*